(12) United States Patent
Altschul et al.

(10) Patent No.: US 11,364,252 B2
(45) Date of Patent: *Jun. 21, 2022

(54) SYSTEM AND METHOD FOR DIAGNOSIS AND TREATMENT

(71) Applicant: Pop Test Oncology LLC, Cliffside Park, NJ (US)

(72) Inventors: Randice Lisa Altschul, Cliffside Park, NJ (US); Neil David Theise, New York City, NY (US); Myron Rapkin, Indianapolis, IN (US); Rebecca O'Brien, Shell Knob, MO (US)

(73) Assignee: Pop Test Oncology, LLC, Clifside Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/392,264

(22) Filed: Aug. 3, 2021

(65) Prior Publication Data

US 2021/0361675 A1 Nov. 25, 2021

Related U.S. Application Data

(60) Division of application No. 16/691,971, filed on Nov. 22, 2019, now Pat. No. 11,116,775, which is a continuation of application No. 16/251,299, filed on Jan. 18, 2019, now Pat. No. 10,537,586, which is a continuation of application No. 16/050,155, filed on Jul. 31, 2018, now Pat. No. 10,231,982, which is a division of application No. 15/854,053, filed on Dec. 26, 2017, now Pat. No. 10,076,528, which is a division of application No. 15/471,123, filed on Mar. 28, 2017, now Pat. No. 9,861,643, which is a division of application No. 15/095,293, filed on Apr. 11, 2016, now Pat. No. 9,636,351, which is a division of application No. 14/802,060, filed on Jul. 17, 2015, now Pat. No. 9,314,473, which is a continuation-in-part of application No. 14/100,714, filed on Dec. 9, 2013, now Pat. No. 9,114,147, which is a division of application No. 13/364,651, filed on Feb. 2, 2012, now Pat. No. 8,658,128.

(60) Provisional application No. 61/462,492, filed on Feb. 3, 2011, provisional application No. 61/463,212, filed on Feb. 14, 2011, provisional application No. 61/465,703, filed on Mar. 23, 2011, provisional application No. 61/518,248, filed on May 3, 2011, provisional application No. 61/519,323, filed on May 20, 2011.

(51) Int. Cl.

| | | |
|---|---|---|
| *A61K 31/58* | (2006.01) |
| *A61K 45/06* | (2006.01) |
| *B65D 75/00* | (2006.01) |
| *B65D 75/36* | (2006.01) |
| *A61J 1/10* | (2006.01) |
| *A61N 5/10* | (2006.01) |
| *A61K 47/10* | (2017.01) |
| *A61K 47/26* | (2006.01) |
| *A61K 47/34* | (2017.01) |
| *A61K 9/08* | (2006.01) |
| *A61K 9/10* | (2006.01) |
| *A61K 9/107* | (2006.01) |
| *A61K 47/42* | (2017.01) |
| *A61K 47/44* | (2017.01) |
| *A61K 31/337* | (2006.01) |
| *C07J 17/00* | (2006.01) |
| *A61K 38/09* | (2006.01) |
| *A61K 9/00* | (2006.01) |
| *A61K 51/00* | (2006.01) |
| *G01N 33/74* | (2006.01) |

(52) U.S. Cl.
CPC ............. *A61K 31/58* (2013.01); *A61J 1/10* (2013.01); *A61K 9/0019* (2013.01); *A61K 9/0053* (2013.01); *A61K 9/08* (2013.01); *A61K 9/10* (2013.01); *A61K 9/107* (2013.01); *A61K 31/337* (2013.01); *A61K 38/09* (2013.01); *A61K 45/06* (2013.01); *A61K 47/10* (2013.01); *A61K 47/26* (2013.01); *A61K 47/34* (2013.01); *A61K 47/42* (2013.01); *A61K 47/44* (2013.01); *A61K 51/00* (2013.01); *A61N 5/1001* (2013.01); *B65D 75/002* (2013.01); *B65D 75/36* (2013.01); *B65D 75/367* (2013.01); *C07J 17/00* (2013.01); *G01N 33/743* (2013.01); *A61N 2005/1091* (2013.01); *A61N 2005/1098* (2013.01); *G01N 2333/575* (2013.01); *G01N 2800/56* (2013.01)

(58) Field of Classification Search
CPC ........ A61K 31/58; A61K 45/06; A61K 47/10; A61K 47/26; A61K 47/34; A61K 9/08; A61K 9/10; A61K 9/107; A61K 47/42; A61K 47/44; A61K 31/337; A61K 38/09; A61K 9/0053; A61K 9/0019; A61K 51/00; B65D 75/002; B65D 75/36; B65D 75/367; A61J 1/10; A61N 5/1001; A61N 2005/1091; A61N 2005/1098; C07J 17/00; G01N 33/743; G01N 2333/575; G01N 2800/56
See application file for complete search history.

(56) References Cited

U.S. PATENT DOCUMENTS

2002/0169152 A1* 11/2002 Belanoff ................ A61K 31/56
514/179

OTHER PUBLICATIONS

Arvanitakis et al. (Arch Neurol.; 61:661-666).*

* cited by examiner

*Primary Examiner* — Shirley V Gembeh
(74) *Attorney, Agent, or Firm* — Abelman, Frayne & Schwab; Stefan Knirr

(57) ABSTRACT

This invention relates the use of cortisol blockers (glucocorticoid receptor [GR] antagonists) for the treating or preventing treatment resistant prostate cancer, treating or preventing neoplasia, and treating or preventing infection related to acute or chronic injury or disease.

1 Claim, 8 Drawing Sheets

SYSTEM AND METHOD FOR DIAGNOSIS AND TREATMENT

CROSS REFERENCE TO RELATED APPLICATIONS

This application is a Divisional of U.S. Ser. No. 16/691,971, filed Nov. 22, 2019, which is a Continuation application of U.S. Ser. No. 16/251,299 filed Jan. 18, 2019, now U.S. Pat. No. 10,537,586, issued Jan. 21, 2020, which is a Continuation application of U.S. Ser. No. 16/050,155 filed Jul. 31, 2018, now U.S. Pat. No. 10,231,982 issued Mar. 19, 2019, which is a Divisional application of U.S. Ser. No. 15/854,053 filed Dec. 26, 2017, now U.S. Pat. No. 10,076,528, issued Sep. 18, 2018, which is a Divisional application of U.S. Ser. No. 15/471,123, filed Mar. 28, 2017, now U.S. Pat. No. 9,861,643 issued Jan. 9, 2018, which is a Divisional application of U.S. Ser. No. 15/095,293, filed Apr. 11, 2016, now U.S. Pat. No. 9,636,351 issued May 2, 2017, which is a Divisional application of U.S. Ser. No. 14/802,060 filed Jul. 17, 2015, now U.S. Pat. No. 9,314,473, issued Apr. 19, 2016, which is a Continuation-in-Part of U.S. Ser. No. 14/100,714 filed Dec. 9, 2013, now U.S. Pat. No. 9,114,117, issued Aug. 25, 2015, which is a Divisional application of U.S. Ser. No. 13/364,651, filed Feb. 2, 2012, now U.S. Pat. No. 8,658,128, issued Feb. 25, 2014, which claims benefit under 35 U.S.C. § 119(e) to U.S. Provisional Patent Application 61/462,492 filed Feb. 3, 2011; U.S. Provisional Patent Application 61/463,212 filed Feb. 14, 2011; U.S. Provisional Patent Application 61/465,703 filed Mar. 23, 2011; U.S. Provisional Patent Application 61/518,248 filed May 3, 2011; and U.S. Provisional Patent Application 61/519,323 filed May 20, 2011, the disclosures of which are incorporated herein by reference in their entirety.

BACKGROUND OF THE INVENTION

1. Field of Invention

This invention relates the use of cortisol blockers (e.g., glucocorticoid receptor [GR] antagonists) for the treating or preventing treatment resistant prostate cancer, treating or preventing neoplasia, and treating or preventing infection related to acute or chronic injury or disease.

2. Description of Related Art

ORG 34517 is one of a class of therapeutic agents designed to block the glucorticoid receptor (GR), acting as an antagonist for endogenous cortisol. Its primary developmental pathway has been as a treatment for neuropsychiatric diseases that are characterized by dysregulated signaling in the hypothalamic-pituitary-adrenal axis, often with higher than normal circulating levels of endogenous cortisol. Of particular note are the phase 2 clinical trials that have been completed for the treatment of psychotic depression. Other possible uses in this disease category which are under investigation include: post-traumatic stress disorder, weight gain in patients requiring long term anti-psychotic medication, hospital delirium of the elderly, etc.

The endogenous glucocorticoids are steroids predominantly produced in the adrenal cortex. Glucocorticoids are important steroids for intermediary metabolism, immune, musculoskeletal, connective tissue and brain function. The main glucocorticoid in the body is cortisol. The production and secretion of cortisol is governed by a complex and highly efficient system that includes the hypothalamus, pituitary and the adrenal glands i.e., hypothalamic-pituitary-adrenal axis (HPA). Cortisol secretion has a circadian release rhythm with peak values in early morning and trough values at midnight.

The production and secretion of the most important glucocorticoid, cortisol, is governed by a complex and highly efficient system that includes the hypothalamus, pituitary and the adrenal glands i.e., hypothalamic-pituitary-adrenal axis. Cortisol secretion is regulated by the suprachiasmatic nucleus of the hypothalamus into a circadian release rhythm. The timing is synchronized with the solar day by dark-light shifts, which normally reflect the habitual sleep-wake pattern. Therefore in healthy persons, the cortisol secretion has a 24-hour circadian pattern with peak serum levels in the early morning, 3-6 hours after onset of sleep, and nadir levels around midnight. Physical and psychological stressors also activate cortisol secretion. Changed patterns of serum cortisol levels have been observed in connection with abnormal adrenocorticotropic hormone (ACTH), levels, clinical depression, psychological stress, and physiological stressors such as hypoglycemia, illness, fever, trauma, surgery, fear, pain, physical exertion, or temperature extremes. Cortisol levels and responsiveness may also differ from normal for elderly individuals and in individuals with autism or Asperger's syndrome.

Glucocorticoids (GCs) such as, in humans, cortisol, perform several important functions. These include participating in the regulation of carbohydrate, protein and fat metabolism by signaling the liver to make glucose and glycogen, the adipose tissues to release lipids and fatty acids into the bloodstream, and the skeletal muscles to release proteins or amino acids into the bloodstream. GCs also decrease bone formation.

GCs also regulate the body's inflammatory response as well. GCs are part of the feedback mechanism in the immune system that inhibits immune activity (i.e., inflammation). GCs cause their effects by binding to the GCR. The activated GCR complex in turn up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression) (Rhen T and Cidlowski J A. NEJM 2005; 353: 1711-23).

GCR antagonist therapy is helpful in patients with abnormally high levels of cortisol (but maintained circadian rhythm), over responsiveness to normal levels, or high night time cortisol levels as a feature of disrupted circadian rhythm. Such altered cortisol physiology may relate to acute or chronic stress (e.g. related to physical or psychological trauma) or as an age related change in elderly individuals. Successful therapeutic use of such agents is thus often dependent on determining circadian cortisol levels (either peak levels during the day, e.g., at noon, or measurements taken every 4 hours or 6 hours over a 24 hour period). This combined system of salivary cortisol quantification as an enabling device for its paired GCR antagonist will identify individuals for whom GCR antagonist therapy has a benefit.

The glucocorticoid receptor (GR) is expressed at high levels in some normal tissues, but not in others. Likewise, malignant tumors of diverse types and sites have variable GR expression. When present in normal or tumor (benign or malignant) tissues, this GR expression may be variously located in some or all of their cellular sub-compartments: 1. stem cells; 2. progenitor (so called "transit amplifying") cell descendents of activated stem cells; and 3. differentiated progeny of activated stem or progenitor cells.

The present invention therefore relates to the use of GR antagonists (e.g., ORG 34517—a relatively specific GR antagonist, RU486—a non-specific GR antagonist, and others), optionally in combination with at least one other agent, for treating or preventing treatment resistant prostate cancer, treating or preventing neoplasia, and/or treating or preventing infection related to acute or chronic injury or disease.

All references cited herein are incorporated herein by reference in their entireties.

BRIEF SUMMARY OF THE INVENTION

The invention provides a method for treating neoplasia characterized by expression of a glucocorticoid receptor, in a patient in need of such treatment, comprising: administering to said patient at least one therapeutically effective neoplasia-treating therapy, and a GCR (glucocorticoid receptor) antagonist selected from the group consisting of ORG 34517, 11-(substituted phenyl)-estra-4,9-diene derivatives, and 11-(substituted phenyl)-estra-4,9-diene derivatives of formula I

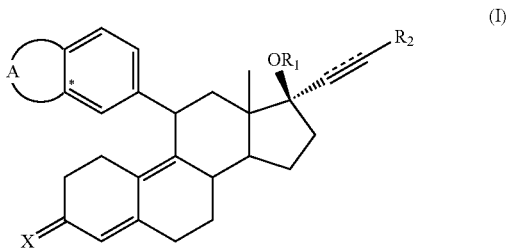

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from ($H_2OH$), O, and NOH; and the interrupted line represents an optional bond, thereby treating said animal or human. The invention provides a method for treating neoplasia characterized by expression of a glucocorticoid receptor wherein the GCR antagonist is ORG34517 ((11β,17β)-11-(1,3-benzodioxol-5-yl)-17-hydroxy-17-(1-propynyl) estra-4,9-dien-3-one) which has the following formula:

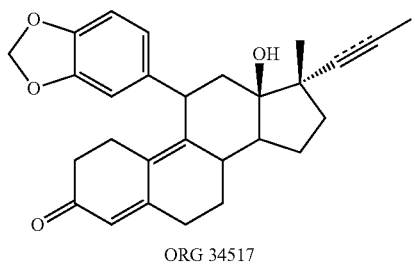

ORG 34517

The invention provides a method for treating neoplasia characterized by expression of a glucocorticoid receptor wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention provides a method for treating neoplasia characterized by expression of a glucocorticoid receptor wherein the neoplasia is chemo-resistant ER/GR+ breast cancer. The invention provides a method for treating neoplasia characterized by expression of a glucocorticoid receptor wherein said neoplasia-treating therapy is radiation. The invention provides a method for treating neoplasia characterized by expression of a glucocorticoid receptor wherein said neoplasia-treating therapy is a radionuclide. The invention provides a method for treating neoplasia characterized by expression of a glucocorticoid receptor wherein said neoplasia treating therapy is selected from the group consisting of X-rays, gamma rays, and other sources of radiation. The invention provides a method for treating neoplasia characterized by expression of a glucocorticoid receptor wherein said neoplasia treating therapy is radiation therapy administered as external beam radiation, wherein the radiation is directed from a remote source. The invention provides a method for treating neoplasia characterized by expression of a glucocorticoid receptor wherein said neoplasia treating therapy is radiation therapy administered as brachytherapy wherein a radioactive source is placed inside the body close to cancer stem cells, cancer cells, and/or a tumor mass. The invention provides a method for treating neoplasia characterized by expression of a glucocorticoid receptor wherein the method comprises administration of a neoplasia treating therapy followed by the administration of the GCR antagonist ORG34517. The invention provides a method for treating neoplasia characterized by expression of a glucocorticoid receptor wherein the method comprises administration of a neoplasia treating therapy and the administration of the GCR antagonist ORG34517 concurrently. The invention provides a method for treating neoplasia characterized by expression of a glucocorticoid receptor wherein the method comprises administration of the GCR antagonist ORG34517 followed by the administration of a neoplasia treating therapy. The invention provides a method for treating neoplasia characterized by expression of a glucocorticoid receptor wherein said neoplasia treating therapy comprises both radiation therapy and an additional neoplasia treating therapy. The invention provides a method for treating neoplasia characterized by expression of a glucocorticoid receptor wherein said additional neoplasia treating therapy is selected from the group consisting of peptides, polypeptides, fusion proteins, nucleic acid molecules, small molecules, mimetic agents, synthetic drugs, inorganic molecules, organic molecules, hormonal therapies, anti-angiogenesis therapies, targeted therapies, biological therapies, immunotherapy, and surgery. The invention provides a method for treating neoplasia characterized by expression of a glucocorticoid receptor wherein the administration of ORG 34517 for GR-blockade, reduces toxicities and side effects when given systemically. The invention provides a method for treating neoplasia characterized by expression of a glucocorticoid receptor wherein the ORG 34517 given systemically through oral or intravenous routes. The invention provides a method for treating neoplasia characterized by expression of a glucocorticoid receptor wherein the ORG 34517 is given to accomplish cure or remission of tumor. The invention provides a method for treating neoplasia characterized by expression of a glucocorticoid receptor wherein the ORG 34517 is given to accomplish reduction of tumor burden to enhance effectiveness of subsequent surgical resection.

The invention provides a method for treating neoplasia in a patient in need of such treatment, the method comprising: a) administering to said patient a therapeutically effective amount of ORG 34517; and b) administering to said patient at least one therapeutically effective neoplasia-treating therapy, thereby treating said patient. The invention provides a method for treating neoplasia wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention provides a method for treating neoplasia wherein the neoplasia is chemo-resistant ER/GR+ breast cancer. The invention provides a method for treating neoplasia wherein said neoplasia treating therapy is radiation. The invention provides a method for treating neoplasia wherein said neoplasia treating therapy is a radionuclide. The invention provides a method for treating neoplasia wherein said neoplasia treating therapy is selected from the group consisting of X-rays, gamma rays, and other sources of radiation. The invention provides a method for treating neoplasia wherein said neoplasia treating therapy is radiation therapy administered as external beam radiation or teletherapy, wherein the radiation is directed from a remote source. The invention provides a method for treating neoplasia wherein said neoplasia treating therapy is radiation therapy administered as internal therapy or brachytherapy wherein a radioactive source is placed inside the body close to cancer stem cells, cancer cells, and/or a tumor mass. The invention provides a method for treating neoplasia wherein the method comprises administration of a neoplasia treating therapy followed by the administration of the GCR antagonist ORG34517. The invention provides a method for treating neoplasia wherein the method comprises administration of a neoplasia treating therapy and the administration of the GCR antagonist ORG34517 concurrently. The invention provides a method for treating neoplasia wherein the method comprises administration of the GCR antagonist ORG34517 followed by the administration of the neoplasia treating therapy. The invention provides a method for treating neoplasia wherein said neoplasia treating therapy comprises both radiation therapy and an additional neoplasia treating therapy. The invention provides a method for treating neoplasia wherein said additional neoplasia treating therapy is selected from the group consisting of peptides, polypeptides, fusion proteins, nucleic acid molecules, small molecules, mimetic agents, synthetic drugs, inorganic molecules, organic molecules, hormonal therapies, anti-angiogenesis therapies, targeted therapies, biological therapies, immunotherapy, and surgery. The invention provides a method for treating neoplasia wherein the neoplasia expresses multidrug resistance genes when GR is activated through binding by endogenous cortisol. The invention provides a method for treating neoplasia wherein the ORG 34517 given systemically through oral or intravenous routes. The invention provides a method for treating neoplasia wherein the ORG 34517 is given to accomplish cure or remission of tumor. The invention provides a method for treating neoplasia wherein the ORG 34517 is given to accomplish reduction of tumor burden to enhance effectiveness of subsequent surgical resection.

BRIEF DESCRIPTION OF THE SEVERAL VIEWS OF THE DRAWING

FIG. 4A shows a blister pack of reagent cartridge units. FIG. 4B shows an exemplary reaction vessel and cap. FIG. 4C shows an exemplary sample carrier. FIG. 4D shows an exemplary reagent 2 (fluorescent ligand) carrier.

FIG. 5A shows an exemplary sample carrier. FIG. 5B shows an exemplary reaction vessel and cap. FIG. 5C shows an exemplary reagent 2 (fluorescent ligand) carrier.

FIG. 6A shows an exemplary sample carrier. FIG. 6B shows an exemplary reagent 2 (fluorescent ligand) carrier.

DETAILED DESCRIPTION OF THE INVENTION

Figure 1:
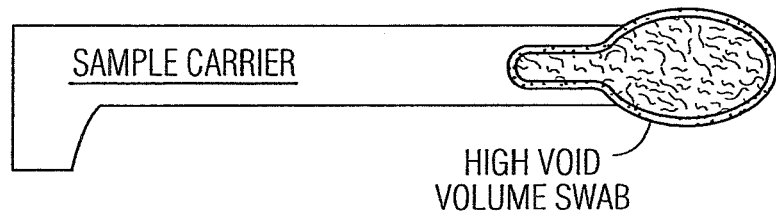
FIG. 1 is an example of a sample carrier.
Figure 2:
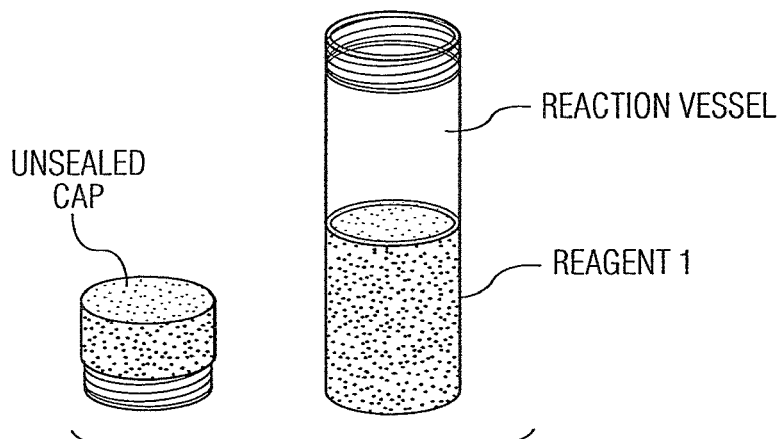
FIG. 2 is an example of glass reaction vessel with reagent one dispensed inside.
Figure 3:
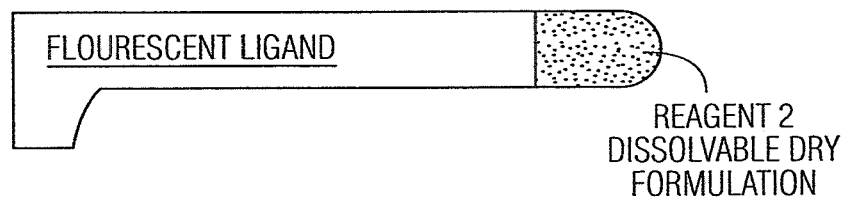
FIG. 3 is an example of a fluorescent ligand reagent two, dry formulation to be dissolved in the reaction vessel.
Figure 4A:
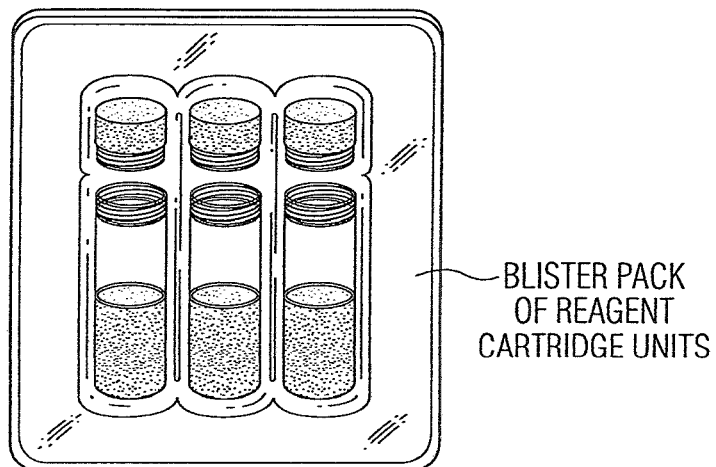
FIGS. 4A through 4D show examples of additional embodiments of the chemistry process configuration.
Figure 4B:
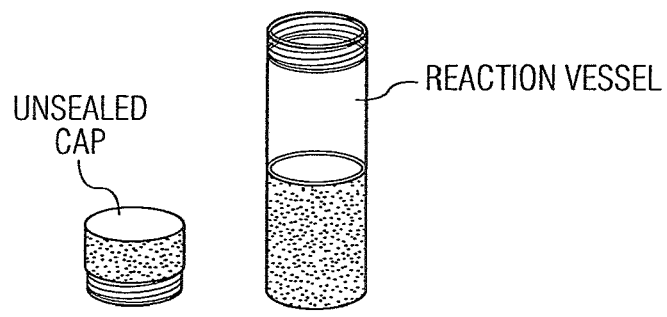
Figure 4C:
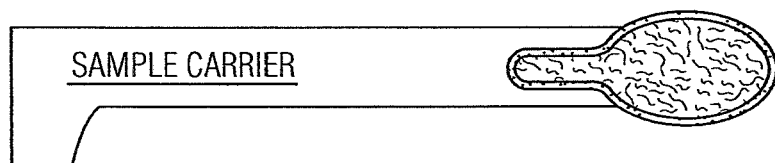
Figure 4D:
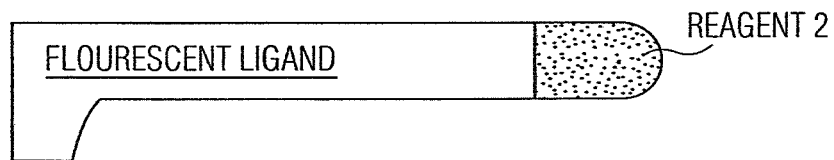
Figure 5A:
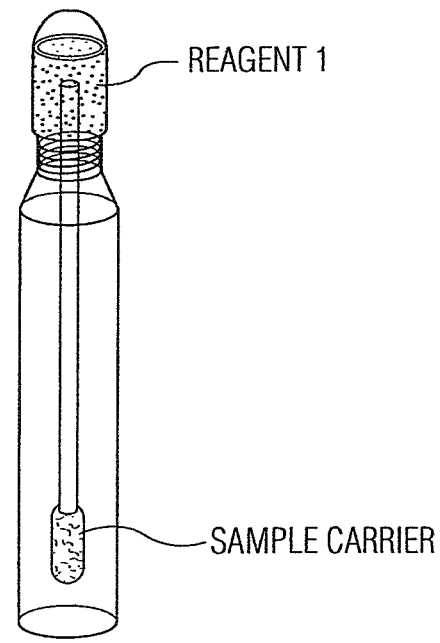
FIGS. 5A through 5C show examples of additional embodiments of the chemistry process configuration.
Figure 5B:
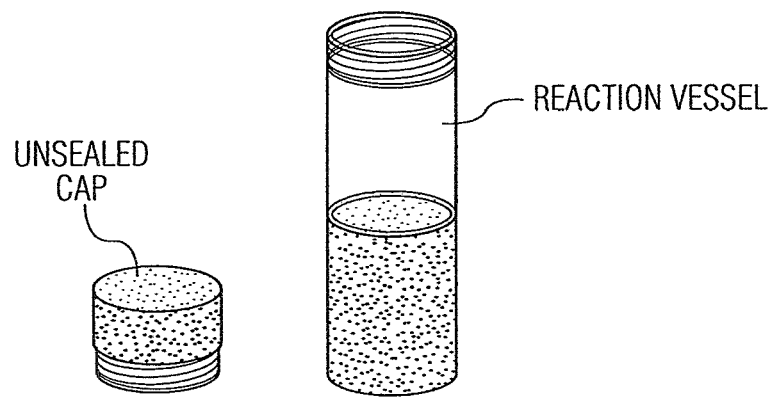
Figure 5C:
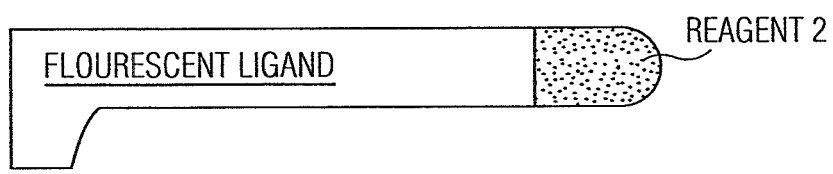
Figure 6A:
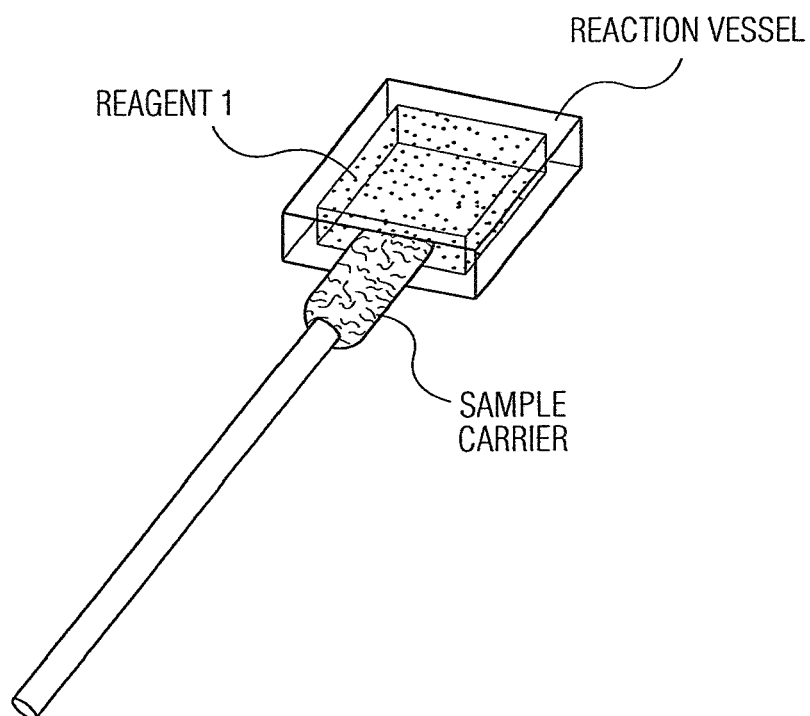
FIGS. 6A and 6B show additional embodiments of chemistry process configuration-plastic cartridge.
Figure 6B:
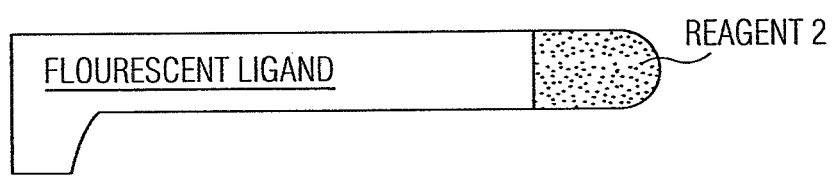
Figure 7:
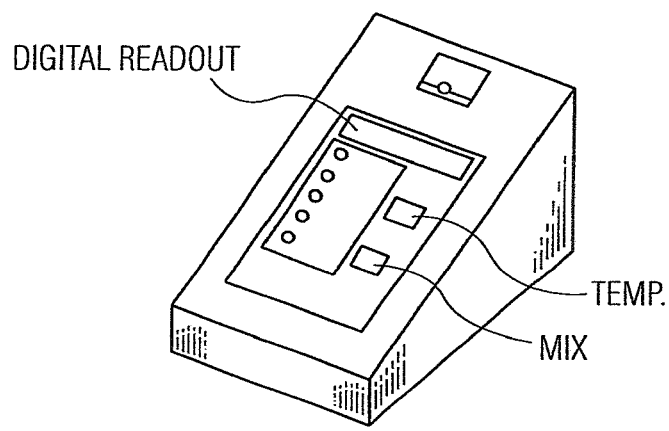
FIG. 7 is an example of a Fluorescence Polarization Reader (DC and battery operated wt.<3 lbs).
Figure 8:
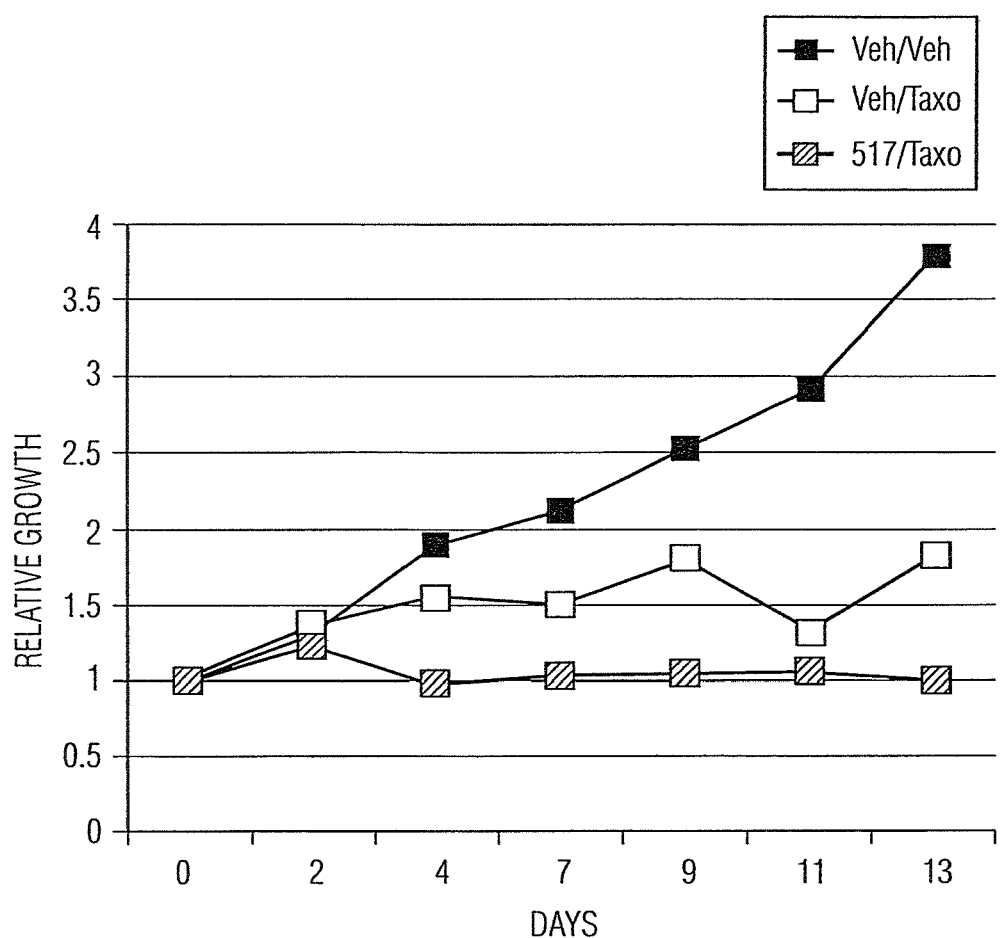
FIG. 8 is Effect of Vehicle (Ethanol/Castor Oil)/Vehicle (Ethanol/Sesame Oil), Vehicle (Ethanol/Castor Oil)/Taxol (10 mg/kg/day) and ORG 34517 (20.5 mg/kg/day)/Taxol (10 mg/kg/day) on relative tumor growth. Compounds are administered day 1-5.
Figure 9:
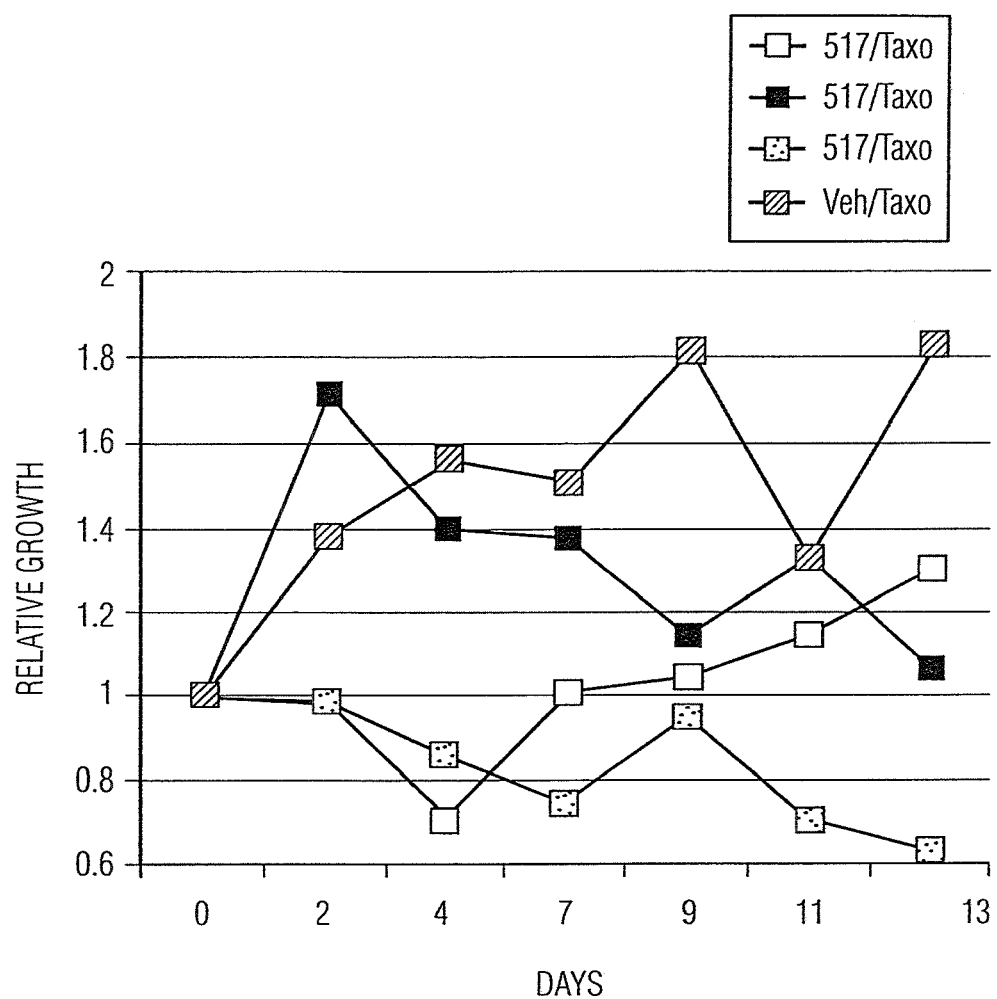
FIG. 9 shows the Effect of Vehicle (Ethanol/Castor Oil)/Taxol (10 mg/kg/day) and ORG 34517 (20.5 mg/kg/day)/Taxol (10 mg/kg/day) on relative tumor growth. The average curve for Veh/Taxo is shown. 517/Taxocurves are show for each individual animal. Compounds are administered day 1-5.
Figure 10:
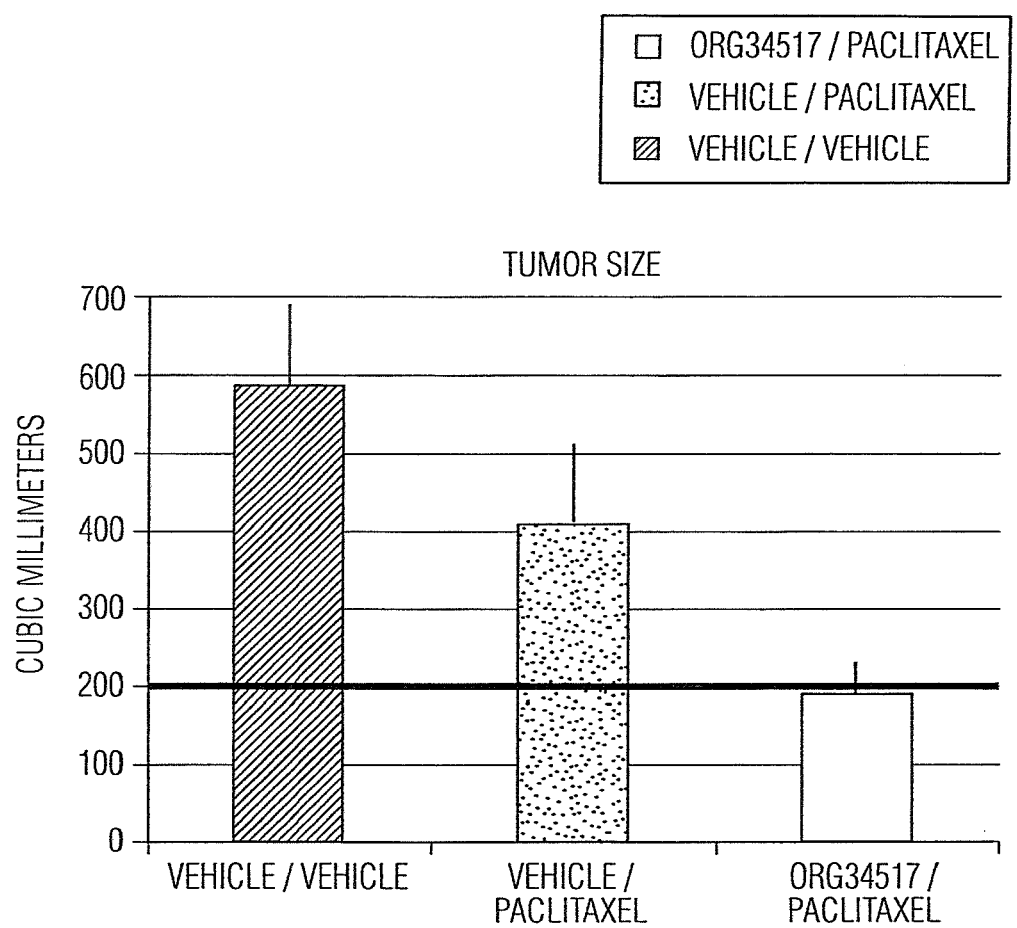
FIG. 10 shows the results of an experiment in which mice were implanted with cultured ER-GR+ human breast cancer cells. As tumor volume in each mouse approached the test threshold of 200 mm3, the mice were randomized to receive intraperitoneal injections of vehicle alone, chemotherapy (Paclitaxel) alone, and chemotherapy and ORG 34517. Each group contained 3 mice. Results show significant differences in attained tumor volume
Figure 11:
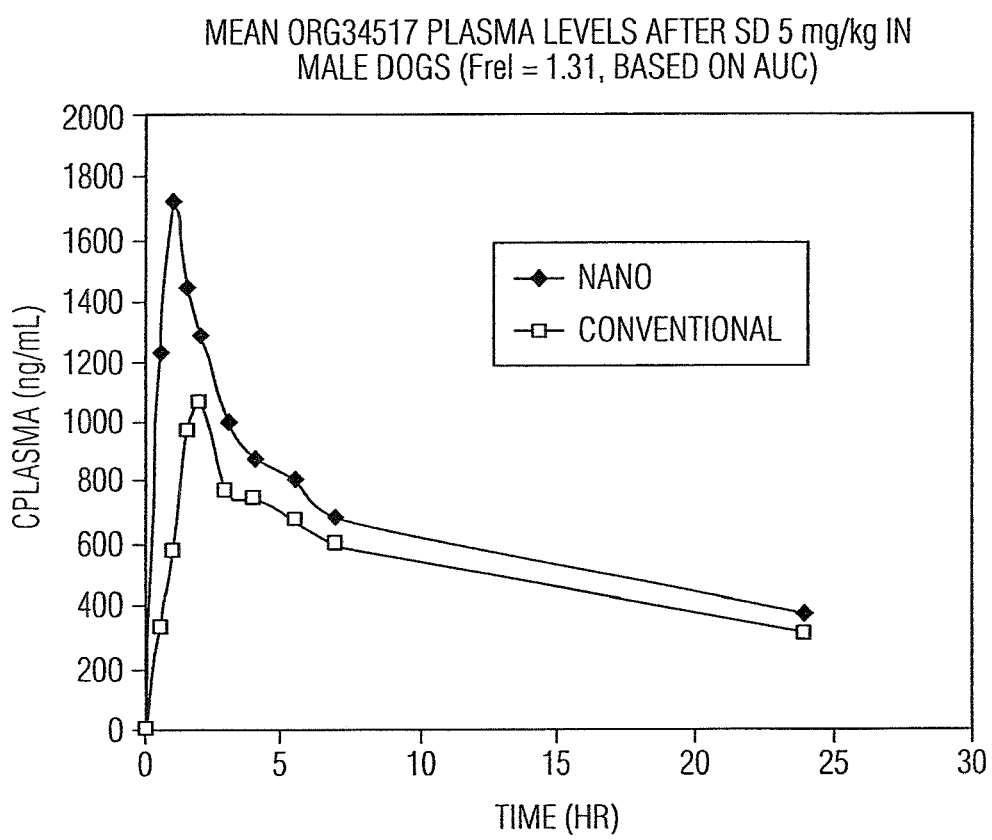
FIG. 11 shows the $AUC_{0-24}$. Two dogs were included in the test. The nanosuspension increases the exposure of (11b,17b)-11-(1,3-benzodioxol-5-yl)-17-hydroxy-17-(1-propynyl)estra-4,9-d-ien-3-one.

The invention is directed to the use of, for example, a glucocorticoid receptor antagonist, optionally in combination with another agent, for treating or preventing treatment resistant prostate cancer, treating or preventing neoplasia, and/or treating or preventing infection related to acute or chronic injury or disease.

As used herein, the term "effective amount" refers to the amount of a therapy that is sufficient to result in the prevention of the development, recurrence, or onset of a disease or condition, such as neoplasia or infection, and one or more symptoms thereof, to enhance or improve the prophylactic effect(s) of another therapy, reduce the severity, the duration of a disease or condition, such as neoplasia or infection, ameliorate one or more symptoms of a disease or condition such as neoplasia or infection, prevent the advancement of a disease or condition, such as neoplasia or infection, cause regression of a disease or condition, such as neoplasia or infection, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, such as neoplasia or infection, or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a disease or condition, such as neoplasia or infection, or one or more symptoms thereof.

As used herein, the terms "treat," "treatment," and "treating" in the context of the administration of a therapy to a subject refer to the reduction or inhibition of the progression and/or duration of a disease or condition, such as neoplasia or infection, the reduction or amelioration of the severity of a disease or condition, such as neoplasia or infection, and/or the amelioration of one or more symptoms thereof resulting from the administration of one or more therapies.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "androgenergic antagonist" refers to agents that can prevent androgens from expressing their biological effects on responsive tissues. These agents alter the androgen pathway by blocking the appropriate receptors, competing for binding sites on the cell's surface, or affecting androgen production. Androgenergic antagonist can be prescribed to treat an array of diseases and disorders. In men, these agents are most frequently used to treat prostate cancer. In women, these agents are used to decrease levels of male hormones causing symptoms of hyperandrogenism. Androgenergic antagonist present in the environment have become a topic of concern. Many industrial chemicals, pesticides and insecticides exhibit antiandrogenic effects. Non-limiting examples of the androgenergic antagonist include, but not limited to, allylestrenol, oxendolone, osaterone acetate, bicalutamide, steroidal, anti-androgergic agents, medroxyprogesterone (MPA), cyproterone, cyproterone acetate (CPA), dienogest, flutamide, nilutamide, spironolactone, 5alpha-reductase inhibitors, dutasteride, finasteride, salts thereof, gold nanoparticles thereof, combinations thereof, and the like. In some embodiments of the present invention, examples of the androgenergic antagonist includes, but not limited to a gold nanoparticle of alpha-bicalutamide, or a gold nanoparticle of beta-bicalutamide.

Glucocorticoid Receptor

The glucocorticoid receptor is widely distributed and expressed in many cultured cell lines, and the control of gene expression by glucocorticoids, therefore, has been widely studied as a model for transcriptional regulation. A number of glucocorticoid-responsive transcription units, including mouse mammary tumor virus (MMTV) (Ringold, et al., 1975; Parks, et al., 1974), mouse and human metallothionein (Eager, et al., 1981; Karin, et al., 1980), rat alpha2M-globulin (Kurtz, et al., 1977) and rat and human growth hormone (Spindler, et al., 1982; Evans, et al., 1982; Robins, et al., 1982) genes have been identified. DNA sequences mediating transcriptional stimulation of several of these genes have been localized. For MMTV, these sequences are discrete genomic regions upstream of the transcriptional start site which appear to exert their actions independently of orientation and position (Chandler, et al., 1983; Ostrowski, et al., 1984). The steroid/receptor complex appears to bind to these regulatory sequences and purified receptor has been used to define the specific binding sites (Govinda, et al., 1982; Scheidereit, et al., 1983; Pfahl, 1982; Payvar, et al., 1983). The ability of the glucocorticoid-responsive element (GRE) to alter its position and orientation yet still maintain promoter inducibility suggests that it resembles the class of cis-acting regulatory sequences termed enhancers (Chandler, et al., 1983). First discovered in viruses and subsequently in cellular genes, these sequences are necessary for efficient transcription in vivo (Laimonis, et al., 1982; Benoist, et al., 1981; Baerji, et al., 1983). It has been suggested that enhancers are recognized by trans-acting factors that mediate regulatory effects by tissue-specific transcriptional control. Although the enhancer factors have not been well characterized, the glucocorticoid receptor may serve as a paradigm for these putative gene activator proteins.

It is generally accepted that the unliganded glucocorticoid receptor (GR) resides in the cytoplasm, and that hormone activation leads both to nuclear accumulation and gene activation. (Gasc, J.-M. & Baulieu, E. E. (1987) in Steroid Hormone Receptors: Their Intracellular Localisation, ed. Clark, C. R. (Ellis Horwood Ltd., Chichester, England), pp. 233-250; Beato, M. (1989) Cell 56, 335-344; Carson-Jurica, M. A., Schrader, W. T. & O'Malley, B. W. (1990) Endocr. Rev. 11, 201-220; Gronemeyer, H. (1993) in Steroid Hormone Action, ed. Parker, M. G. (Oxford University Press, New York), pp. 94-117; Tsai, M. J. & O'Malley, B. W. (1994) Annu. Rev. Biochem. 63, 451-486; Akner, G., Wikstrom, A. C. & Gustafsson, J. A. (1995) J. Steroid Biochem. Mol. Biol. 52, 1-16), and references therein. However, the mechanisms involved in nuclear translocation and targeting of steroid receptors to regulatory sites in chromatin have been poorly understood. It has previously been difficult to discriminate between the ability of a given receptor mutant, or a given receptor/ligand combination, to participate in the separate processes of receptor activation, nuclear translocation, sequence-specific binding, and promoter activation.

The glucocorticoid receptor (GR) is expressed in a subset of both ERalpha-positive and -negative human breast cancers as well as in some ovarian cancers. In vitro and in vivo experiments suggest that activation of the GR in ER-negative pre-malignant breast epithelial and cancer cells initiates cell survival pathways under stress conditions that normally induce significant cell death (e.g. chemotherapy, radiation, growth factor deprivation).

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisolone.

Glucocorticoid Receptor Antagonists

The composition and methods of the invention may make use of glucocorticoid receptor antagonists. Glucocorticoid receptor antagonists bind to the receptor and prevent glucocorticoid receptor agonists from binding and eliciting GR mediated events, including transcription. RU486 is an example of a non-selective glucocorticoid receptor antagonist.

Compounds having high glucocorticoid receptor binding affinity and, in addition, high in vivo anti-glucocorticoid activity, while having, for example, low androgenic and progestagenic activities are disclosed in U.S. Pat. No. 6,011, 025, incorporated herein by reference in its entirety. ORG 34517 is an example of a compound with high glucocorticoid receptor binding affinity while having low androgenic and progestagenic activities.

It has been found that 11-(substituted phenyl)-estra-4,9-diene derivatives of formula I

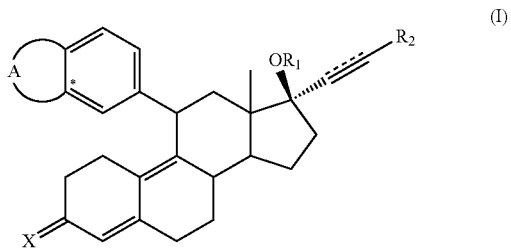

wherein
A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from ($H_2$OH), 0, and NOH; and the interrupted line represents an optional bond, show specific and high glucocorticoid receptor binding affinity and are highly active in vivo showing predominant anti-glucocorticoid activity.

The compounds lack appreciable affinity for mineralocorticoid, progesterone, estrogen and androgen receptors, indicating a clean side effect profile.

The 11-(substituted phenyl)-estra-4,9-diene derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures.

Preferred compounds according to this invention are 11-(substituted phenyl) estra-4,9-diene derivatives, wherein the heteroatom(s) are (is) O, the 5- or 6-membered ring being optionally substituted with one or more fluorine atoms; R1 is H; and X is O or NOH. More preferred compounds are 11-(substituted phenyl) estra-4,9-diene derivatives wherein A is a residue of a 5-membered ring. Particularly preferred are 11-(substituted phenyl) estra-4,9-diene derivatives wherein A contains 2 heteroatoms being O.

Especially preferred are 11-(substituted phenyl) estra-4, 9-diene derivatives wherein R2 is methyl and the interrupted line represents a bond.

The most preferred compound is (11β,17β)-11-(1,3-benzodioxol-5-yl)-17-hydroxy-17-(1-propynyl) estra-4,9-dien-3-one (ORG 34517).

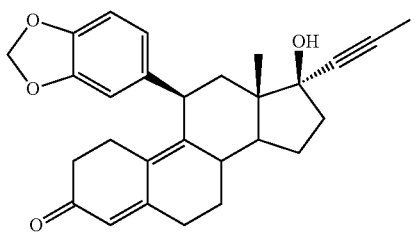

ORG 34517

The term halogen means a fluorine, chlorine, bromine or iodine atom. Fluorine is the preferred halogen in ring A and when R2 is halogen, chlorine is preferred.

The terms (1-4C)alkyl and (1-8C)alkyl, as used in the definitions of R1 and R2, respectively, mean alkyl groups having 1-4 and 1-8 carbon atoms, respectively, for example methyl, ethyl, propyl, isopropyl, butyl, sec-butyl, tert-butyl, pentyl, neopentyl, hexyl, octyl.

The 11-(substituted phenyl)-estra-4,9-diene derivatives according to the present invention can be prepared by a process wherein a compound of formula II

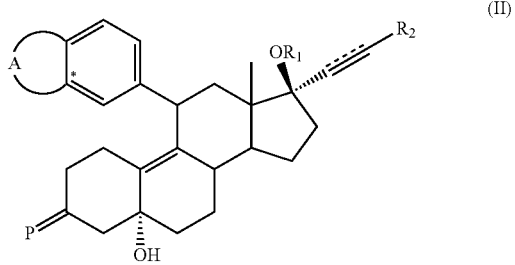

wherein A, R2 and the interrupted line have the meanings as previously defined, R1 is H, and P is a protected keto-group, is dehydrated and deprotected, after which the 17β-OH is optionally esterified by reaction with an appropriate carboxylic acid to give a derivative wherein R1 is 1-oxo(1-4C) alkyl, and optionally the 3-oxo group is converted into the corresponding 3-hydroxy- or 3-oxime derivative. The 3-oxo group can be reduced to form the 3-hydroxy-derivative by using a suitable reducing agent, such as sodium borohydride. The 3-oxime derivatives can be prepared by hydroxylamine treatment in a suitable solvent, like pyridine.

The derivatives of formula II may be prepared according to well known methods described and used for the preparation of steroids.

A suitable process for the preparation of derivatives of formula II starts from estra-4,9-diene-3,17-dione. Selective reduction of the 17-keto group to 17β-OH, 17α-H, e.g. with sodium borohydride, followed by protection of the 3-keto group, e.g., by ketalisation with ethyleneglycol, triethylorthoformate and p-toluenesulfonic acid, and oxidation of the 17-hydroxy group, e.g. with pyridinium chlorochromate, provides the 3-ketoprotected estra-5(10),9(11)-diene-3,17-dione. Alkynylation at the 17-position (yielding a 17α-alkynyl,17β-OH derivative), followed by epoxidation of the 5(10) double bond, e.g. with hydrogen peroxide, trifluoroacetophenone, and pyridine in dichloromethane according to the method as disclosed in European patent application EP 0 298 020, provides the 3-ketoprotected 5α,10α-epoxy-17α-alkynyl-17β-hydroxy-estr-9(11)-ene-3-one.

Subsequently, compounds of formula II are formed from this epoxide derivative, for example by reaction with an organometallic compound of the formula

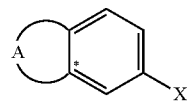

wherein X is a (alkali)metal, like lithium, or a magnesiumhalide, preferably magnesium bromide.

Suitable protective groups and methods to remove these groups are known in the art, for example from T. W. Green: Protective Groups in Organic Synthesis (Wiley, N Y, 1981). Particularly suitable protective groups for the protection of keto groups are acetals, e.g. 1,2-ethylene ketal.

The specificity of ORG 34517 for GR blockade, without significant cross-binding to other related steroidal hormone receptors (such as those for estrogen and progesterone), eliminates the likelihood of significant toxicities and side effects. Indeed, none were identified in all the substantial phase I and phase II clinical trials that already have been performed with the compound. Because the drug is envisioned as being used in limited dosing over time, coordinated with the intermittent dosing strategies typical for chemotherapeutic agents, the GR blockade also would not lead to significant alteration of HPA-axis functioning, with rapid restitution of the HPA-axis to baseline following dosing.

Androgen Receptor Antagonists

The compositions and methods of the invention may also make use of one or more androgen receptor antagonists, such as in a combination with the glucocorticoid receptor antagonist of the invention. For example, the invention provides with at least one glucocorticoid receptor antagonist in combination with at least one androgen receptor antagonist, such as for example, ARN 509 (4-{7-[6-Cyano-5-(trifluoromethyl)-3-pyridinyl]-8-oxo-6-thioxo-5,7-diaz-aspiro[3.4]oct-5-yl}-2-fluoro-N-methylbenzamide). ARN-509 is a novel androgen receptor (AR) antagonist for the treatment of castration-resistant prostate cancer (CRPC). ARN-509 inhibits AR nuclear translocation and AR binding to androgen response elements and, unlike bicalutamide, does not exhibit agonist properties in the context of AR overexpression.

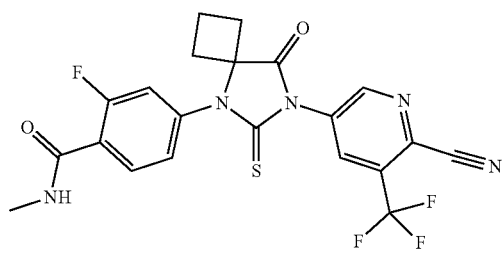

ARN-509

Another exemplary antiadrogen is bicalutamide, which has the chemical name (R,S)—N-(4-cyano-3-(4-fluorophenylsulfonyl)-2-hydroxy-2-methyl-3-(triflu-oromethyl)propanamide, Flutamide (brand name Eulexin), nilutamide (brand names Anandron and Nilandron) and bicalutamide (brand name Casodex) are nonsteroidal, "pure" antiandrogens; 5-alpha-reductase inhibitors such as finasteride (brand names Proscar and Propecia), dutasteride (brand name Avodart), bexlosteride, izonsteride, turosteride, and episteride are antiandrogenic as they prevent the conversion of testosterone to dihydrotestosterone (DHT); Spironolactone (brand names Aldactone and Spirotone), a synthetic 17-spirolactone corticosteroid; Cyproterone acetate (brand names Androcur, Climen, Diane 35, and Ginette 35) is a synthetic steroid, a potent antiandrogen that also possesses progestational properties. Hydroxyflutamide.

In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the androgen receptor antagonist is enzalutamide (marketed as Xtandi®, Astellas Pharma US, Inc.), also known as and referred to herein as MDV3100, having the chemical name 4-(3-(4-cyano-3-(trifluoromethyl)phenyl)-5,5-dimethyl-4-oxo-2-thioxoimida-zolidin-1-yl)-2-fluoro-N-methylbenzamide.

The compositions and methods of the invention may also make use of one or more androgen receptor antagonist, such as in a combination with the glucocorticoid receptor antagonist of the invention. The androgen receptor antagonist may be selected from the group consisting of, for example, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, and combinations thereof.

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The compositions of the present invention are combinations of GCRAs and, for example, androgen receptor antagonists, which can be used to alleviate any condition associated with inappropriate activation of the androgen receptor. In addition to prostate cancer, other examples of such conditions include acne, hirsutism, seborrhea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborhhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compositions of the invention may also be used topically to decrease seborrhea production and more specifically to alleviate hyperseborrhoea (oily skin), which can be used topically alleviate acne.

Poly(ADP-Ribose) Polymerase (PARP)

The compositions and methods of the invention may also make use of one or more PARP inhibitors, such as in a combination with the glucocorticoid receptor antagonist of the invention. The poly (ADP-ribose) polymerase (PARP) is also known as poly (ADP-ribose) synthase and poly ADP-ribosyltransferase. PARP catalyzes the formation of mono- and poly (ADP-ribose) polymers which can attach to cellular proteins (as well as to itself) and thereby modify the activities of those proteins. The enzyme plays a role in regulation of transcription, cell proliferation, and chromatin remodeling (see D'amours et al., Biochem., 342: 249268, 1999).

Poly(ADP-ribose)polymerase has an essential role in facilitating DNA repair, controlling RNA transcription, mediating cell death, and regulating immune response. These actions make PARP inhibitors targets for a broad spectrum of disorders. (Virag L., et al., Pharmacol. Rev. 2002 54(3):375-429). In various preclinical cancer models and human clinical trials, PARP inhibitors have been shown to potentiate radiation and chemotherapy by increasing apoptosis of cancer cells, limiting tumor growth, decreasing metastasis, and prolonging the survival of tumor-bearing subjects. (WO 2007-084532; Donawho C. K., et al., Clin Cancer Res 2007 13(9):2728-37; Kummar S., et al., J Clin Oncol. 2009 27(16):2705-11).

PARP comprises an N-terminal DNA binding domain, an automodification domain, and a C-terminal catalytic domain. Various cellular proteins interact with PARP. The N-terminal DNA binding domain contains two zinc finger motifs. Transcription enhancer factor-1 (TEF-1), retinoid X receptor a, DNA polymerase a, X-ray repair cross-complementing factor-1 (XRCC1) and PARP itself interact with PARP in this domain. The automodification domain contains a BRCT motif, one of the protein-protein interaction modules. This motif is originally found in the C-terminus of BRCA1 (breast cancer susceptibility protein 1) and is present in various proteins related to DNA repair, recombination and cell-cycle checkpoint control. POU-homeodomain-containing octamer transcription factor-1 (Oct-1), YinYang (YY)1, and ubiquitinconjugating enzyme 9 (ubc9) could interact with this BRCT motif in PARP.

More than 15 members of the PARP family of genes are present in the mammalian genome. PARP family proteins and poly(ADP-ribose) glycohydrolase (PARG), which degrades poly(ADP-ribose) to ADP-ribose, are involved in a variety of cell regulatory functions including DNA damage response and transcriptional regulation and associated with carcinogenesis and the biology of cancer.

Several PARP family proteins have been identified. Tankyrase has been found as an interacting protein of telomere regulatory factor 1 (TRF-1) and is involved in telomere regulation. Vault PARP (VPARP) is a component in the vault complex, which acts as a nuclear-cytoplasmic transporter. PARP-2, PARP-3 and 2,3,7,8-tetrachlorodibenzo-p-dioxin inducible PARP (TiPARP) have also been identified. Therefore, poly(ADP-ribose) metabolism could be related to a variety of cell regulatory functions.

A member of this gene family is PARP-1. The PARP-1 gene product is expressed at high levels in the nuclei of cells and is dependent upon DNA damage for activation. It is believed that PARP-1 binds to DNA single or double-stranded breaks (DSBs) through an amino-terminal DNA-binding domain. The binding activates the carboxy-terminal catalytic domain and results in the formation of polymers of ADP-ribose on target molecules. PARP-1 is itself a target of poly ADP-ribosylation by virtue of a centrally located automodification domain. The ribosylation of PARP-1 causes dissociation of the PARP-1 molecules from the DNA. The entire process of binding, ribosylation, and dissociation occurs very rapidly. It has been suggested that this transient binding of PARP-1 to sites of DNA damage results in the recruitment of DNA repair machinery or may act to suppress the recombination long enough for the recruitment of repair machinery.

The source of ADP-ribose for the PARP reaction is nicotinamide adenosine dinucleotide (NAD). NAD is synthesized in cells from cellular ATP stores and thus high levels of activation of PARP activity can rapidly lead to depletion of cellular energy stores. It has been demonstrated that induction of PARP activity can lead to cell death that is correlated with depletion of cellular NAD and ATP pools. PARP activity is induced in many instances of oxidative stress or during inflammation. For example, during reperfusion of ischemic tissues reactive nitric oxide is generated and nitric oxide results in the generation of additional reactive oxygen species including hydrogen peroxide, peroxynitrate, and hydroxyl radical. These latter species can directly damage DNA and the resulting damage induces activation of PARP activity. Frequently, it appears that sufficient activation of PARP activity occurs such that the cellular energy stores are depleted and the cell dies. A similar mechanism is believed to operate during inflammation when endothelial cells and pro-inflammatory cells synthesize nitric oxide, which results in oxidative DNA damage in surrounding cells and the subsequent activation of PARP activity. The cell death that results from PARP activation is believed to be a major contributing factor in the extent of tissue damage that results from ischemia-reperfusion injury or from inflammation.

PARP (poly-ADP ribose polymerase) participates in a variety of DNA-related functions including cell proliferation, differentiation, apoptosis, DNA repair and also effects on telomere length and chromosome stability (d'Adda di Fagagna et al., Nature Gen., 23(1): 76-80, 1999). Oxidative stress-induced overactivation of PARP consumes NAD+ and consequently ATP, culminating in cell dysfunction or necrosis. This cellular suicide mechanism has been implicated in the pathomechanism of cancer, stroke, myocardial ischemia, diabetes, diabetes-associated cardiovascular dysfunction, shock, traumatic central nervous system injury, arthritis, colitis, allergic encephalomyelitis, and various other forms of inflammation. PARP has also been shown to associate with and regulate the function of several transcription factors.

PARP Inhibitors

Suitable PARP inhibitors for use in the compositions and methods of the invention include, but are not limited to, 4-[[3-[4-(cyclopropanecarbonyl)piperazine-1-carbonyl]-4-fluorophenyl]-met-hyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (ABT-888), 8-Fluoro-2-{4-[(methylamino)methyl]-phenyl}-1,3,4,5-tetrahydro-6H-azepino-[5,4,3-cd]indol-6-one (AG014699), 4-methoxy-carbazole (CEP 9722), 2-[4-[(3S)-piperidin-3-yl]phenyl]indazole-7-carboxamide hydrochloride (MK 4827), and 3-aminobenzamide, or a pharmaceutically acceptable salt thereof.

In some embodiments, the Glucocorticoid receptor antagonists, e.g., an ORG-34517 composition described herein, is administered in combination with a poly ADP-ribose polymerase (PARP) inhibitor (e.g., BSI 201, Olaparib (AZD-2281), ABT-888, AG014699, CEP 9722, MK 4827, KU-0059436 (AZD2281), LT-673, 3-aminobenzamide). Other example PARP inhibitors include, i.e., pharmacological inhibitors of the enzyme poly ADP ribose polymerase (PARP). Suitable PARP inhibitors may be iniparib, olaparib, rucaparib, veliparib, or CEP 9722. Current PARP inhibitors in clinical trials include: Iniparib (Sanofi), Olaparib (Astra-Zeneca), Rucaparib (Pfizer), Veliparib (Abbott), CEP-9722 (Cephalon), MK4827 (Merck), BMN-673 (Biomarin), among others.

Treatment Resistant Prostate Cancer

The invention provides a method for treating and/or preventing treatment resistant prostate cancer in a patient in need of such treatment and/or prevention, comprising: administering to the patient therapeutically effective amounts of a GCR (glucocorticoid receptor) antagonist as exemplified herein, in combination with, for example, a neoplasia treating agent, including, for example, an androgen receptor (AR) antagonist. Prostate cancer is the most commonly diagnosed cancer in men and the second leading cause of death from cancer in North American and European males. New therapeutic approaches are needed to prevent and treat advanced and metastatic prostate cancer. Nutritional factors, particularly high intake of protein and calcium, as well as metabolic syndrome, are known to modify prostate cancer risk and progression, but the molecular mechanisms linking nutrition to prostate cancer are unknown. There are also links between prostate cancer and bone metabolism. Osteocalcin (OC), which encodes a vitamin-K dependent hormone predominantly produced by osteoblasts/osteocytes in bone, which functions to regulate energy metabolism, is also ectopically expressed by some prostate cancers that have a propensity to metastasize to bone. Polymorphisms in OC are also associated with prostate cancer progression. Recent evidence has also identified a correlation between the bone transcription factor Runx2 and advanced stages of prostate and breast cancer, as evidenced by the effects of depletion of Runx2 by RNA interference to inhibit migration and invasive properties of the cells and prevent metastatic bone disease. It is possible that OC secreted by bone may directly target prostate cancer cells. Finally, androgen deprivation therapy is the principal medical therapy for prostate cancer, but androgen ablation often becomes ineffective in controlling prostate cancer progression and castration-resistant metastatic disease, particularly to bone, becomes incurable. There is growing evidence for the presence of a putative membrane androgen sensing receptor that mediates the rapid, non-genomic effects of androgens, which also might be involved in prostate cancer growth and metastasis. Regardless, clues to possible new molecular targets to regulate prostate cancer growth and progression may be discovered from a better understanding of the molecular mechanisms underlying nutritional risk factors, OC effects and androgen resistance in prostate cancer.

Neoplasia, Cancer, Tumors, Proliferative Diseases, Malignancies and their Metastases The invention provides a method for treating neoplasia in a patient in need of such treatment, comprising: administering to the patient therapeutically effective amounts of a GCR (glucocorticoid receptor) antagonist as exemplified herein, in combination with, for example, a neoplasia treating agent. The term "neoplasia" as used herein refers also to tumors, proliferative diseases, malignancies and their metastases. Examples for cancer diseases are Adenocarcinomas of the head and neck (including salivary glands and oral cavity), gastrointestinal tract (including pharynx, esophagus, stomach, small intestine, large intestine, anus), lung, liver (including hepatocellular carcinoma, cholangiocarcinoma, and mixed tumors), extrahepatic biliary tract and gallbladder, pancreas (including ductal and acinar types), genitourinary tracts (ovaries, fallopian tubes, endometrium, cervix, and vagina, ureters, urinary bladder, testicles, epididymis, prostate), and skin adnexa; squamous cell carcinomas of the head and neck (including salivary glands and oral cavity), gastrointestinal tract (including pharynx, esophagus, anus), lung, intrahepatic and extrahepatic biliary tree (including gallbladder), pancreas, genitourinary tracts (including endometrium, cervix, vagina, ureters, urinary bladder, testicles, epididymis, prostate), and skin adnexa; germ cell tumors (including malignant teratoma, embryonal carcinoma, struma ovarii, yolk sac tumor, seminoma, choriocarcinoma); sarcomas (including leiomyosarcomas, rhabdomyosarcomas, angiosarcomas, hemangioendotheliomas, liposarcomas, chondosarcomas, fibrosarcomas, Ewing sarcoma, malignant nerve sheathe tumors, alveolar soft part sarcomas, clear cell sarcomas, synovial sarcoma, osteosarcomas); malignancies of the central nervous system (including astrocytomas, oligodendroglioma, glioblastoma, medulloblastoma); salivary gland malignancies (including adenoid cystic carcinoma, adenosquamous carcinoma, clear cell carcinoma, cystadenocarcinoma, mucoepidermoid carcinoma); mixed type carcinomas (including hepatocellular-cholangiocarcinomas, carcinosarcomas, mixed adenoneurondocrine carcinomas, adenosquamous carcinomas); hepatocellular carcinoma; blastic malignancies (including hepatoblastoma, neuroblastoma, ganglioneuroblastoma, nephroblastoma); renal cell carcinomas; neuroendocrine carcinomas; thyroid carcinomas (including papillary, follicular, medullary, anaplastic carcinomas); parathyroid carcinomas, pituitary gland carcinomas, adrenal gland carcinomas (including adrenocortical carcinomas, pheochromocytoma), and combinations thereof.

Treating or Preventing Infection Related to Acute or Chronic Injury or Disease

The invention provides a method for treating or preventing infection related to acute or chronic injury or disease in a patient in need of such treatment, comprising: administering to the patient therapeutically effective amounts of a GCR (glucocorticoid receptor) antagonist as exemplified herein, in combination with, for example, another agent. In particular, the invention has application to minimize life-threatening complications of persons suffering injury to cells, tissues or organs resulting from burns, shock, stroke, heart attack or other physical events, including complications from surgical or clinical interventions, as a consequence of trauma. Injured soldiers on the battlefield or civilians at a natural disaster site or injured from a terrorist attack are situations where such treatment may be useful.

The invention applies to protecting, preserving or stabilizing key organs such as the heart and brain, other neuronal tissues and cells, renal tissue, lung tissue, muscle tissue, liver and other tissues of the body.

In one form, the invention provides a method of reducing injury to the cells, tissues or organs of a body following trauma by administering a composition to the body following trauma including: (i) a glucocorticoid receptor antagonist; and optionally (ii) another pharmaceutical agent.

The term "trauma" is used herein in its broadest sense and refers to a serious or critical injury, wound or shock to the body. Trauma may be caused by unexpected physical damage (or injury) to the body as a result of, for example, transport or industrial accidents, birth, surgery, heart attack, stroke, burns, complications due to surgery or other medical interventions etc. Trauma may result from injury to a body, both in a hospital or out of hospital. Trauma is often associated with trauma medicine practiced in hospital (such as in hospital emergency rooms), during emergency transport or at out-of-hospital environments where a trauma has occurred, such as domestic or industrial accidents, transport accidents, the battlefield, and terrorist attacks. In many cases, trauma therapy may also include resuscitation therapy. Exemplary injuries include, for example, burns, shock, stroke, heart attack or other physical events, including complications from surgical or clinical interventions, as a consequence of trauma. Injured soldiers on the battlefield or civilians at a natural disaster site or injured from a terrorist attack are situations where such treatment may be useful.

The invention provides a method for treating or preventing infection related to acute or chronic injury or disease wherein said method comprises administering to a patient in need of such therapy at least one glucocorticoid receptor antagonist in a therapeutically effective amount.

The activities of GR agonists and their alteration of cellular functions are variable, depending on complex intracellular molecular signaling that are cell and tissue specific. Amongst the cells that have glucocorticoid receptors are stem and progenitor cells of all tissues and organs of the body.

Thus, binding of such molecules to normative, "in-tissue" stem cells and the progeny of these stem cells, so-called "transit amplifying" progenitor cells, results in variable, cell and tissue specific effects, inhibitory or enhancing of stem and progenitor cell functions, including activation, proliferation, migration and differentiation all of which are dependent on the tissue/organ in question.

GR antagonists, such as, for example, ORG34517, will thus block the effects of GR-agonists in tissue specific fashion, enhancing stem/progenitor cell functioning in some, inhibiting it in others. GR-antagonists will have beneficial effects in specific clinical settings where regenerative medicine approaches to disease and wound healing may be of use, including: enhanced post-transplant functioning of autologous stem cell transplants (dependent on tissue of origin and/or target tissue).

Attenuation of the peri-surgical effects of catabolic stress hormones related to surgical or other physical traumas (e.g. combat wounds), wherein the acute or chronic injury or disease is selected from the group consisting of vascular events, stroke, cardiac arrest, acute limb infarction accident/battle field trauma, traumatic limb, hip, brain injuries, post-surgical trauma, major orthopedic, thoracic, abdominal, neurological surgeries.

Systemic GR blockade will be inappropriate, but direct application of ORG34517 to site of injury/wounding, either topically (for example, to prevent wound dehiscence) or by direct injection or intravascular infusion (for visceral organ injuries) will be beneficial.

CNS Injury

The invention provides a method for treating or preventing CNS injury in a patient in need of such treatment, comprising: administering to the patient therapeutically effective amounts of a GCR (glucocorticoid receptor) antagonist as exemplified herein, in combination with, for example, another agent. Conditions suitable for treatment according to this invention include, for example, seizure disorders, pain syndromes, neurodegenerative diseases (including motor neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillian-Barre syndrome, dysproteinemias, transthyretin-induced neuropathies, and carpal tunnel syndrome).

As used herein, seizure disorders include complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, mesial temporal lobe epilepsy, nocturnal frontal lobe epilepsy, progressive epilepsy with mental retardation, and progressive myoclonic epilepsy, as well as seizures associated with CNS mass lesions.

Pain syndromes include, for example, headaches (e.g., migraine, tension, and cluster), acute pain, chronic pain, neuropathic pain, nociceptive pain, central pain and inflammatory pain, drug-induced neuropathic pain, causalgia, complex regional pain syndrome types I and II, and reflex sympathetic dystrophy (RSDS).

Neurodegenerative diseases include Alzheimer's disease, Parkinson's Disease, multiple sclerosis, Huntington's Disease, ALS, spinal muscular atrophy, muscular dystrophies prion-related diseases, cerebellar ataxia, Friedrich's ataxia, SCA, Wilson's disease, RP, Gullain Barre syndrome, Adrenoleukodystrophy, Menke's Sx, cerebral autosomal dominant arteriopathy with subcortical infarcts (CADASIL), Charcot Marie Tooth diseases, neurofibromatosis, von-Hippel Lindau, Fragile X, spastic paraplegia, tuberous sclerosis complex, Wardenburg syndrome, spinal motor atrophies, Tay-Sachs, Sandoff disease, familial spastic paraplegia, myelopathies, radiculopathies, encephalopathies associated with trauma, radiation, drugs and infection, and disorders of the sympathetic nervous system (e.g., Shy Drager (familial dysautonomia), diabetic neuropathy, drug-induced and alcoholic neuropathy).

Dementias include Alzheimer's disease, Parkinson's disease, Pick's disease, fronto-temporal dementia, vascular dementia, normal pressure hydrocephalus, Huntington's disease, and MCI.

Cerebrovascular conditions amenable to treatment according to the present invention include cerebrovascular disease and strokes (e.g., thrombotic, embolic, thromboembolic, hemorrhagic [including AVM and berry aneurysms], venoconstrictive, and venous).

Included in movement disorders are Parkinson's disease, dystonias, benign essential tremor, tardive dystonia, tardive dyskinesia, and Tourette's syndrome.

Brain trauma as used herein includes traumatic brain and spinal cord injuries as well as brain injuries from radiation.

Cranial nerve disorders include trigeminal neuropathy, trigeminal neuralgia, Menier's syndrome, glossopharangela neuralgia, dysphagia, dysphonia, cranial nerve palsies and Bell's palsy.

Neuropsychiatric disorders include panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence/addiction (e.g., alcohol, psychostimulants (e.g., crack, cocaine, speed, meth), opioids, and nicotine), and drug-induced psychiatric disorders.

Other disease neuropathies that may be treated with the compositions and methods described herein include Guillain-Barre, diabetes associated neuropathies, dysproteinemias, transthyretin-induced neuropathies, neuropathy associated with HIV, herpes viruses (including herpes zoster) or other viral infection, neuropathy associated with Lyme disease, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, post-meningitis syndrome, post-polio syndrome, prion diseases, and radiation associated neuropathic syndromes.

Other diseases amenable to treatment with the present invention include fatigue syndromes (e.g., chronic fatigue syndrome and fibromyalgia), ataxic syndromes, olivopontoicerebellar degeneration, striatonigral degeneration, and axonic brain damage.

The present invention is particularly useful in the treatment of neuropsychiatric disorders such as depression, agitation, anxiety, seizure disorders such as grand mal seizures, status epilepticus, migraine pain treatment and prophylaxis, Alzheimer's disease, Parkinson's disease, and traumatic brain and spinal cord injury.

Also, the higher doses enabled by the present invention are expected to be of particular importance for dementias including Alzheimer's disease, Parkinson's disease, and vascular dementia, pain syndromes, including headaches and migraines, seizure disorders, movement disorders, and brain trauma.

Furthermore, the ease of use and convenience of a dosage form provided developed to be delivered at once per day or less frequent administration at a therapeutically effective quantity from the onset of therapy is of value in the treatment of dementias including Alzheimer's disease and Parkinson's disease, seizure disorders, pain syndromes, and cerebrovascular conditions.

Enhanced Memory and/or Performance

Situational stress can lead to elevated circulating levels of cortisol which, in turn, can impair short term memory formation. For example, student exam periods in high school, college, as well as graduate school and professional certification and licensing exams can lead to such stress and, therefore, to a self-defeating, cortisol associated deficit in learning that may impair formation of study-based memories and lead to poorer than expected test results. The present invention is particularly useful in the treatment and/or prevention of short term memory performance by, for example, single or sequential dosing with a glucocorticoid blocking compound or composition of the invention, before and during the examination study period, that will prevent suppression of short term memory formation and improve study and subsequent examination performance.

Immunomodulatory Effect

The inventive pharmaceutical composition may additionally contain one or more auxiliary substances in order to further increase its immunomodulatory effect, for example, ORG 34517 (Myvotum) in combination with immune system regulators (e.g., IL-1R antagonist) for prevention of post-traumatic or disease-associated systemic immunosuppression at high risk for bacterial infections (e.g., wound infections, pneumonia, colitis, pyelonephritis, hepatic and splenic abscesses) and sepsis. New compositions and methods are provided which advantageously employ compounds having a newly defined immune modulating function, or which have the ability to mimic that immune modulating function, or a combination of such compounds. For the purposes of the present disclosure, the terms "immune mimic," "immune modulating," "immune modulator," "immune modulation," "immune control," "immune inhibition," "immune suppressor," and the like, refer in most instances to the newly identified cancer cell growth (i.e., proliferation) inhibitory effect of the secretory immune system (i.e., dimeric/polymeric IgA and pentameric IgM) that is mediated by a newly identified Poly-Ig receptor or Poly-Ig-like receptor (also classified as an Fc-like receptor), and not to the usual antibody/antigen recognition based immune function of the immune system. In this context, the terms "immune modulation" or "immune enhancement" refer especially to the modulation or enhancement of these cell growth inhibitory immunoglobulins of the secretory immune system. The term "immune mimic" refers to a substance (e.g., tamoxifen) that can function in a similar manner to an immunoglobulin inhibitor of cell growth. In some instances, however, reference is also made herein to "natural immune inhibition," "immune enhancer," "immune modulator," "immune system," "immune therapy," and "immune response," and the like, in which the conventional meanings of those terms are intended and the context so indicates, especially when prior art methods, compounds and compositions are described. Hereinafter, an indication has been made in appropriate instances whether a conventional definition or the "new" meaning, or both, is intended. A synergistic action of the compounds of the invention, e.g., ORG 34517 or a derivative thereof as defined according to the present invention, and of an auxiliary substance, which may be optionally contained in the inventive pharmaceutical composition as described above, is preferably achieved thereby. Depending on the various types of auxiliary substances, various mechanisms can come into consideration in this respect. In general, it is possible to use as auxiliary substance any agent that influences the immune system in the manner of a "danger signal" (LPS, GP96, etc.) or cytokines, such as GM-CSF, which allow for an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-1 receptor antagonist, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

The inventive pharmaceutical composition can also additionally or alternatively contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Immunoinflammatory Disorder

Another aspect of the present invention is directed to the use of the inventive compound and/or combination as a therapeutic agent for the prophylaxis and/or treatment of immunoinflammatory disorder. The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; allergic rhinitis; allergic intraocular inflammatory diseases, antineutrophil cytoplasmic antibody (ANCA)-associated small-vessel vasculitis; ankylosing spondylitis; arthritis, asthma; atherosclerosis; atopic dermatitis; autoimmune hepatitis; autoimmune hemolytic anemia; autoimmune hepatitis; Behcet's disease; Bell's palsy; bullous pemphigoid; cerebral ischemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; focal segmental glomerulosclerosis; giant cell arteritis; gout; gouty arthritis; graft versus host disease; hand eczema; Henoch-Schonlein purpura; herpes gestationis; hirsutism; idiopathic cerato-scleritis; idiopathic pulmonary fibrosis; idiopathic thrombocytopenic purpura; immune thrombocytopenic purpura inflammatory bowel or gastrointestinal disorders, inflammatory dermatoses; lichen planus; lupus nephritis; lymphomatous tracheobronchitis; macular edema; multiple sclerosis; myasthenia gravis; myositis; non-specific fibrosing lung disease; osteoarthritis; pancreatitis; pemphigoid gestationis; pemphigus vulgaris; periodontitis; polyarteritis nodosa; polymyalgia rheumatica; pruritus scroti; pruritis/inflammation, psoriasis; psoriatic arthritis; pulmonary histoplasmosis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; transplant-rejection and transplant-rejection-related syndromes; tuberculosis; type-1 diabetes; ulcerative colitis; uveitis; vasculitis; and Wegener's granulomatosis.

As used herein, "non-dermal inflammatory disorders" include, for example, rheumatoid arthritis, inflammatory bowel disease, asthma, and chronic obstructive pulmonary disease. By "dermal inflammatory disorders" or "inflammatory dermatoses" is meant an inflammatory disorder selected from psoriasis, guttate psoriasis, inverse psoriasis, pustular psoriasis, erythrodermic psoriasis, acute febrile neutrophilic dermatosis, eczema, asteatotic eczema, dyshidrotic eczema, vesicular palmoplantar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, pityriasis rosea, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifugum, erythema dyschromicum perstans, erythema multiforme, granuloma annulare, hand dermatitis, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

By "proliferative skin disease" is meant a benign or malignant disease that is characterized by accelerated cell division in the epidermis or dermis. Examples of proliferative skin diseases are psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis. As will be appreciated by one skilled in the art, a particular disease, disorder, or condition may be characterized as being both a proliferative skin disease and an inflammatory dermatosis. An example of such a disease is psoriasis.

Symptoms and signs of inflammation associated with specific conditions include: rheumatoid arthritis: —pain, swelling, warmth and tenderness of the involved joints; generalized and morning stiffness; insulin-dependent diabetes mellitus-insulitis; this condition can lead to a variety of complications with an inflammatory component, including: —retinopathy, neuropathy, nephropathy; coronary artery disease, peripheral vascular disease, and cerebrovascular disease; autoimmune thyroiditis: —weakness, constipation, shortness of breath, puffiness of the face, hands and feet, peripheral edema, bradycardia; multiple sclerosis: —spasticity, blurry vision, vertigo, limb weakness, paresthesias; uveoretinitis: —decreased night vision, loss of peripheral vision; lupus erythematosus: —joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis; scleroderma: —Raynaud's disease; swelling of the hands, arms, legs and face; skin thickening; pain, swelling and stiffness of the fingers and knees, gastrointestinal dysfunction, restrictive lung disease; pericarditis; renal failure; other arthritic conditions having an inflammatory component such as rheumatoid spondylitis, osteoarthritis, septic arthritis and polyarthritis: —fever, pain, swelling, tenderness; other inflammatory brain disorders, such as meningitis, Alzheimer's disease, AIDS dementia encephalitis: —photophobia, cognitive dysfunction, memory loss; other inflammatory eye inflammations, such as retinitis: —decreased visual acuity; inflammatory skin disorders, such as, eczema, other dermatites (e.g., atopic, contact), psoriasis, burns induced by UV radiation (sun rays and similar UV sources): —erythema, pain, scaling, swelling, tenderness; inflammatory bowel disease, such as Crohn's disease, ulcerative colitis: —pain, diarrhea, constipation, rectal bleeding, fever, arthritis; asthma: —shortness of breath, wheezing; other allergy disorders, such as allergic rhinitis: —sneezing, itching, runny nose conditions associated with acute trauma such as cerebral injury following stroke-sensory loss, motor loss, cognitive loss; heart tissue injury due to myocardial ischemia: —pain, shortness of breath; lung injury such as that which occurs in adult respiratory distress syndrome: —shortness of breath, hyperventilation, decreased oxygenation, pulmonary infiltrates; inflammation accompanying infection, such as sepsis, septic shock, toxic shock syndrome: —fever, respiratory failure, tachycardia, hypotension, leukocytosis; other inflammatory conditions associated with particular organs or tissues, such as: (i) nephritis (e.g., glomerulonephritis): —oliguria, abnormal urinalysis; (ii) inflamed appendix: —fever, pain, tenderness, leukocytosis; (iii) gout: —pain, tenderness, swelling and erythema of the involved joint, elevated serum and/or urinary uric acid; (iv) inflamed gall bladder: —abdominal pain and tenderness, fever, nausea, leukocytosis; (v) congestive heart failure: —shortness of breath, rales, peripheral edema; (vi) Type II diabetes: —end organ complications including cardiovascular, ocular, renal, and peripheral vascular disease; (vii) lung (pulmonary) fibrosis: —hyperventilation, shortness of breath, decreased oxygenation; (viii) vascular disease, such as atherosclerosis and restenosis: —pain, loss of sensation, diminished pulses, loss of function; and (ix) alloimmunity leading to transplant rejection: —pain, tenderness, fever.

Neurodegenerative Disease

Another aspect of the present invention is directed to the use of the inventive compound and/or combination as a therapeutic agent for the prophylaxis and/or treatment of Neurodegenerative Disease.

The present invention also relates generally to the fields of neurology and psychiatry and to methods of protecting the cells of a mammalian central nervous system from damage or injury. Injuries or trauma of various kinds to the central nervous system (CNS) or the peripheral nervous system (PNS) can produce profound and long-lasting neurological and/or psychiatric symptoms and disorders. One form that this can take is the progressive death of neurons or other cells of the central nervous system (CNS), i.e., neurodegeneration or neuronal degeneration. Neuronal degeneration as a result of, for example; Alzheimer's disease, multiple sclerosis, cerebral-vascular accidents (CVAs)/stroke, traumatic brain injury, spinal cord injuries, degeneration of the optic nerve, e.g., ischemic optic neuropathy or retinal degeneration and other central nervous system disorders is an enormous medical and public health problem by virtue of both its high incidence and the frequency of long-term sequelae. Animal studies and clinical trials have shown that amino acid transmitters (especially glutamate), oxidative stress and inflammatory reactions contribute strongly to cell death in these conditions. Upon injury or upon ischemic insult, damaged neurons release massive amounts of the neurotransmitter glutamate, which is excitotoxic to the surrounding neurons. Glutamate is a negatively charged amino acid that is an excitatory synaptic transmitter in the mammalian nervous system. Although the concentration of glutamate can reach the millimolar range in nerve terminals its extracellular concentration is maintained at a low level to prevent neurotoxicity. It has been noted that glutamate can be toxic to neurons if presented at a high concentration. The term "excitotoxicity" has been used to describe the cytotoxic effect that glutamate (and other such excitatory amino acids) can have on neurons when applied at high dosages.

Patients with injury or damage of any kind to the central (CNS) or peripheral (PNS) nervous system including the retina may benefit from neuroprotective methods. This nervous system injury may take the form of an abrupt insult or an acute injury to the nervous system as in, for example, acute neurodegenerative disorders including, but not limited to; acute injury, hypoxia-ischemia or the combination thereof resulting in neuronal cell death or compromise. Acute injury includes, but is not limited to, traumatic brain injury (TBI) including, closed, blunt or penetrating brain trauma, focal brain trauma, diffuse brain damage, spinal cord injury, intracranial or intravertebral lesions (including, but not limited to, contusion, penetration, shear, compression or laceration lesions of the spinal cord or whiplash shaken infant syndrome). In addition, deprivation of oxygen or blood supply in general can cause acute injury as in hypoxia and/or ischemia including, but not limited to, cerebrovascular insufficiency, cerebral ischemia or cerebral infarction (including cerebral ischemia or infarctions originating from embolic occlusion and thrombosis, retinal ischemia (diabetic or otherwise), glaucoma, retinal degeneration, multiple sclerosis, toxic and ischemic optic neuropathy, reperfusion following acute ischemia, perinatal hypoxic-ischemic injury, cardiac arrest or intracranial hemorrhage of any type (including, but not limited to, epidural, subdural, subarachnoid or intracerebral hemorrhage).

Trauma or injury to tissues of the nervous system may also take the form of more chronic and progressive neurodegenerative disorders, such as those associated with progressive neuronal cell death or compromise over a period of time including, but not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases (amyotrophic lateral sclerosis), multiple sclerosis, degenerative ataxias, cortical basal degeneration, ALS-Parkinson's-dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease or spinocerebellar ataxia type 3 and olivopontocerebellar degenerations, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome) or prion diseases (including, but not limited to Creutzfeld-Jakob disease, Gerstmann-Strussler-Scheinker disease, Kuru disease or fatal familial insomnia).

In addition, trauma and progressive injury to the nervous system can take place in various psychiatric disorders, including but not limited to, progressive, deteriorating forms of bipolar disorder or schizoaffective disorder or schizophrenia, impulse control disorders, obsessive compulsive disorder (OCD), behavioral changes in temporal lobe epilepsy and personality disorders.

In one preferred embodiment the compounds and/or compositions of the invention would be used to provide neuroprotection in disorders involving trauma and progressive injury to the nervous system in various psychiatric disorders. These disorders would be selected from the group consisting of; schizoaffective disorder, schizophrenia, impulse control disorders, obsessive compulsive disorder (OCD) and personality disorders.

In addition, trauma and injury make take the form of disorders associated with overt and extensive memory loss including, but not limited to, neurodegenerative disorders associated with age-related dementia, vascular dementia, diffuse white matter disease (Binswanger's disease), dementia of endocrine or metabolic origin, dementia of head trauma and diffuse brain damage, dementia pugilistica or frontal lobe dementia, including but not limited to Pick's Disease.

Other disorders associated with neuronal injury include, but are not limited to, disorders associated with chemical, toxic, infectious and radiation injury of the nervous system including the retina, injury during fetal development, prematurity at time of birth, anoxic-ischemia, injury from hepatic, glycemic, uremic, electrolyte and endocrine origin, injury of psychiatric origin (including, but not limited to, psychopathology, depression or anxiety), injury from peripheral diseases and plexopathies (including plexus palsies) or injury from neuropathy (including neuropathy selected from multifocal, sensory, motor, sensory-motor, autonomic, sensory-autonomic or demyelinating neuropathies (including, but not limited to Guillain-Barre syndrome or chronic inflammatory demyelinating polyradiculoneuropathy) or those neuropathies originating from infections, inflammation, immune disorders, drug abuse, pharmacological treatments, toxins, trauma (including, but not limited to compression, crush, laceration or segmentation traumas), metabolic disorders (including, but not limited to, endocrine or paraneoplastic), Charcot-Marie-Tooth disease (including, but not limited to, type 1a, 1b, 2, 4a or 1-X linked), Friedreich's ataxia, metachromatic leukodystrophy, Refsum's disease, adrenomyeloneuropathy, ataxia-telangiectasia, Djerine-Sottas (including, but not limited to, types A or B), Lambert-Eaton syndrome or disorders of the cranial nerves).

Further indications are cognitive disorders. The term "cognitive disorder" shall refer to anxiety disorders, delirium, dementia, amnestic disorders, dissociative disorders, eating disorders, mood disorders, schizophrenia, psychotic disorders, sexual and gender identity disorders, sleep disorders, somatoform disorders, acute stress disorder, obsessive-compulsive disorder, panic disorder, posttraumatic stress disorder, specific phobia, social phobia, substance withdrawal delirium, Alzheimer's disease, Creutzfeldt-Jakob disease, head trauma, Huntington's disease, HIV disease, Parkinson's disease, Pick's disease, learning disorders, motor skills disorders, developmental coordination disorder, communication disorders, phonological disorder, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, pica, rumination disorder, tic disorders, chronic motor or vocal tic disorder, Tourette's disorder, elimination disorders, encopresis, enuresis, selective mutism, separation anxiety disorder, dissociative amnesia, depersonalization disorder, dissociative fugue, dissociative identity disorder, anorexia nervosa, bulimia nervosa, bipolar disorders, schizophreniform disorder, schizoaffective disorder, delusional disorder, psychotic disorder, shared psychotic disorder, delusions, hallucinations, substance-induced psychotic disorder, orgasmic disorders, sexual pain disorders, dyspareunia, vaginismus, sexual dysfunction, paraphilias, dyssomnias, breathing-related sleep disorder, circadian rhythm sleep disorder, hypersomnia, insomnia, narcolepsy, dyssomnia, parasomnias, nightmare disorder, sleep terror disorder, sleepwalking disorder, parasomnia, body dysmorphic disorder, conversion disorder, hypochondriasis, pain disorder, somatization disorder, alcohol related disorders, amphetamine related disorders, caffeine related disorders, cannabis related disorders, cocaine related disorders, hallucinogen related disorders, inhalant related disorders, nicotine related disorders, opioid related disorders, phencyclidine-related disorder, abuse, persisting amnestic disorder, intoxication, withdrawal.

The term "bipolar and clinical disorders" shall refer to adjustment disorders, anxiety disorders, delirium, dementia, amnestic and other cognitive disorders, disorders usually first diagnosed in infancy (e.g.), childhood, or adolescence, dissociative disorders (e.g. dissociative amnesia, depersonalization disorder, dissociative fugue and dissociative identity disorder), eating disorders, factitious disorders, impulse-control disorders, mental disorders due to a general medical condition, mood disorders, other conditions that may be a focus of clinical attention, personality disorders, schizophrenia and other psychotic disorders, sexual and gender identity disorders, sleep disorders, somatoform disorders, substance-related disorders, generalized anxiety disorder (e.g. acute stress disorder, posttraumatic stress disorder), panic disorder, phobia, agoraphobia, obsessive-compulsive disorder, stress, acute stress disorder, anxiety neurosis, nervousness, phobia, posttraumatic stress disorder, posttraumatic stress disorder (PTSD), abuse, obsessive-compulsive disorder (OCD), manic depressive psychosis, specific phobias, social phobia, adjustment disorder with anxious features.

Examples for disorders usually first diagnosed in infancy, childhood, or adolescence are: mental retardation, learning disorders, mathematics disorder, reading disorder, disorder of written expression, motor skills disorders, developmental coordination disorder, communication disorders, expressive language disorder, phonological disorder, mixed receptive-expressive language disorder, stuttering, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, feeding disorder of infancy or early childhood, pica, rumination disorder, tic disorders, chronic motor or vocal tic disorder, Tourette's syndrome, elimination disorders, encopresis, enuresis, selective mutism, separation anxiety disorder, reactive attachment disorder of infancy or early childhood, stereotypic movement disorder.

Examples for substance-related disorders are: alcohol related disorders, amphetamine related disorders, caffeine related disorders, cannabis related disorders, cocaine related disorders, hallucinogen related disorders, inhalant related disorders, nicotine related disorders, opioid related disorders, psychotic disorder, psychotic disorder, phencyclidine-related disorder, abuse, persisting amnestic disorder, anxiety disorder, persisting dementia, dependence, intoxication, intoxication delirium, mood disorder, psychotic disorder, withdrawal, withdrawal delirium, sexual dysfunction, sleep disorder.

The term "neuroprotection" as used herein shall mean; inhibiting, preventing, ameliorating or reducing the severity of the dysfunction, degeneration or death of nerve cells, axons or their supporting cells in the central or peripheral nervous system of a mammal, including a human. This includes the treatment or prophylaxis of a neurodegenerative disease; protection against excitotoxicity or ameliorating the cytotoxic effect of a compound (for example, a excitatory amino acid such as glutamate; a toxin; or a prophylactic or therapeutic compound that exerts an immediate or delayed cytotoxic side effect including but not limited to the immediate or delayed induction of apoptosis) in a patient in need thereof.

The term "a patient in need of treatment with a neuroprotective drug" as used herein will refer to any patient who currently has or may develop any of the above syndromes or disorders, or any disorder in which the patient's present clinical condition or prognosis could benefit from providing neuroprotection to prevent the development, extension, worsening or increased resistance to treatment of any neurological or psychiatric disorder.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluations.

In some embodiments this invention provides methods of neuroprotection. In certain embodiments, these methods comprise administering a therapeutically effective amount of the composition and/or combination of the invention to a patient who has not yet developed overt, clinical signs or symptoms of injury or damage to the cells of the nervous system but who may be in a high risk group for the development of neuronal damage because of injury or trauma to the nervous system or because of some known predisposition either biochemical or genetic or the finding of a verified biomarker of one or more of these disorders.

Thus, in some embodiments, the methods and compositions of the present invention are directed toward neuroprotection in a subject who is at risk of developing neuronal damage but who has not yet developed clinical evidence. This patient may simply be at "greater risk" as determined by the recognition of any factor in a subject's, or their families, medical history, physical exam or testing that is indicative of a greater than average risk for developing neuronal damage. Therefore, this determination that a patient may be at a "greater risk" by any available means can be used to determine whether the patient should be treated with the methods of the present invention.

Accordingly, in an exemplary embodiment, subjects who may benefit from treatment by the methods and the composition and/or combination of this invention can be identified using accepted screening methods to determine risk factors for neuronal damage. These screening methods include, for example, conventional work-ups to determine risk factors including but not limited to: for example, head trauma, either closed or penetrating, CNS infections, bacterial or viral, cerebrovascular disease including but not limited to stroke, brain tumors, brain edema, cysticercosis, porphyria, metabolic encephalopathy, drug withdrawal including but not limited to sedative-hypnotic or alcohol withdrawal, abnormal perinatal history including anoxia at birth or birth injury of any kind, cerebral palsy, learning disabilities, hyperactivity, history of febrile convulsions as a child, history of status epilepticus, family history of epilepsy or any seizure related disorder, inflammatory disease of the brain including lupus, drug intoxication either direct or by placental transfer, including but not limited to cocaine poisoning, parental consanguinity, and treatment with medications that are toxic to the nervous system including psychotropic medications.

The determination of which patients may benefit from treatment with a neuroprotective drug in patients who have no clinical signs or symptoms may be based on a variety of "surrogate markers" or "biomarkers".

As used herein, the terms "surrogate marker" and "biomarker" are used interchangeably and refer to any anatomical, biochemical, structural, electrical, genetic or chemical indicator or marker that can be reliably correlated with the present existence or future development of neuronal damage. In some instances, brain-imaging techniques, such as computer tomography (CT), magnetic resonance imaging (Mill) or positron emission tomography (PET), can be used to determine whether a subject is at risk for neuronal damage. Suitable biomarkers for the methods of this invention include, but are not limited to: the determination by Mill, Conn. or other imaging techniques, of sclerosis, atrophy or volume loss in the hippocampus or overt mesial temporal sclerosis (MTS) or similar relevant anatomical pathology; the detection in the patient's blood, serum or tissues of a molecular species such as a protein or other biochemical biomarker, e.g., elevated levels of ciliary neurotrophic factor (CNTF) or elevated serum levels of a neuronal degradation product; or other evidence from surrogate markers or biomarkers that the patient is in need of treatment with a neuroprotective drug.

It is expected that many more such biomarkers utilizing a wide variety of detection techniques will be developed in the future. It is intended that any such marker or indicator of the existence or possible future development of neuronal damage, as the latter term is used herein, may be used in the methods of this invention for determining the need for treatment with the compounds and methods of this invention.

A determination that a subject has, or may be at risk for developing, neuronal damage would also include, for example, a medical evaluation that includes a thorough history, a physical examination, and a series of relevant bloods tests. It can also include an electroencephalogram (EEG), CT, MM or PET scan. A determination of an increased risk of developing neuronal damage or injury may also be made by means of genetic testing, including gene expression profiling or proteomic techniques. For psychiatric disorders that may be stabilized or improved by a neuroprotective drug, e.g., bipolar disorder, schizoaffective disorder, schizophrenia, impulse control disorders, etc. the above tests may also include a present state exam and a detailed history of the course of the patients symptoms such as mood disorder symptoms and psychotic symptoms over time and in relation to other treatments the patient may have received over time, e.g., a life chart. These and other specialized and routine methods allow the clinician to select patients in need of therapy using the methods and formulations of this invention. In some embodiments of the present invention compounds and/or compostions suitable for use in the practice of this invention will be administered either singly or concomitantly with at least one or more other compounds or therapeutic agents, e.g., with other neuroprotective drugs or antiepileptic drugs, anticonvulsant drugs. In these embodiments, the present invention provides methods to treat or prevent neuronal injury in a patient. The method includes the step of; administering to a patient in need of treatment, an effective amount of the compounds and/or compositions disclosed herein in combination with an effective amount of one or more other compounds or therapeutic agents that have the ability to provide neuroprotection or to treat or prevent seizures or epileptogenesis or the ability to augment the neuroprotective effects of the compounds of the invention.

As used herein the term "combination administration" of a compound, therapeutic agent or known drug with the combination of the present invention means administration of the drug and the one or more compounds at such time that both the known drug and/or combination will have a therapeutic effect. In some cases this therapeutic effect will be synergistic. Such concomitant administration can involve concurrent (i.e. at the same time), prior, or subsequent administration of the drug with respect to the administration of the composition and/or combination of the present invention. A person of ordinary skill in the art would have no difficulty determining the appropriate timing, sequence and dosages of administration for particular drugs of the present invention.

The said one or more other compounds or therapeutic agents may be selected from compounds that have one or more of the following properties: antioxidant activity; NMDA receptor antagonist activity, augmentation of endogenous GABA inhibition; NO synthase inhibitor activity; iron binding ability, e.g., an iron chelator; calcium binding ability, e.g., a Ca (II) chelator; zinc binding ability, e.g., a Zn (II) chelator; the ability to effectively block sodium or calcium ion channels, or to open potassium or chloride ion channels in the CNS of a patient.

Heart and Vascular Disease

Another aspect of the present invention is directed to the use of the inventive compound and/or combination as a therapeutic agent for the prophylaxis and/or treatment of heart disease. Heart disease is a general term used to describe many different heart conditions. For example, coronary artery disease, which is the most common heart disease, is characterized by constriction or narrowing of the arteries supplying the heart with oxygen-rich blood, and can lead to myocardial infarction, which is the death of a portion of the heart muscle. Heart failure is a condition resulting from the inability of the heart to pump an adequate amount of blood through the body. Heart failure is not a sudden, abrupt stop of heart activity but, rather, typically develops slowly over many years, as the heart gradually loses its ability to pump blood efficiently. Risk factors for heart failure include coronary artery disease, hypertension, valvular heart disease, cardiomyopathy, disease of the heart muscle, obesity, diabetes, and/or a family history of heart failure.

Examples of cardiovascular diseases and disorders are: aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, cardiac hypertrophy, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, Sneddon syndrome, superior vena cava syndrome, syndrome X, tachycardia, Takayasu's arteritis, hereditary hemorrhagic telangiectasia, telangiectasis, temporal arteritis, tetralogy of Fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome. Vascular diseases are often the result of decreased perfusion in the vascular system or physical or biochemical injury to the blood vessel.

Peripheral vascular disease (PVD) is defined as a disease of blood vessels often encountered as narrowing of the vessels of the limbs. There are two main types of these disorders, functional disease which doesn't involve defects in the blood vessels but rather arises from stimuli such as cold, stress, or smoking, and organic disease which arises from structural defects in the vasculature such as atherosclerotic lesions, local inflammation, or traumatic injury. This can lead to occlusion of the vessel, aberrant blood flow, and ultimately to tissue ischemia.

One of the more clinically significant forms of PVD is peripheral artery disease (PAD). PAD is often treated by angioplasty and implantation of a stent or by artery bypass surgery. Clinical presentation depends on the location of the occluded vessel. For example, narrowing of the artery that supplies blood to the intestine can result in severe postprandial pain in the lower abdomen resulting from the inability of the occluded vessel to meet the increased oxygen demand arising from digestive and absorptive processes. In severe forms the ischemia can lead to intestinal necrosis. Similarly, PAD in the leg can lead to intermittent pain, usually in the calf, that comes and goes with activity. This disorder is known as intermittent claudication (IC) and can progress to persistent pain while resting, ischemic ulceration, and even amputation.

Peripheral vascular disease is also manifested in atherosclerotic stenosis of the renal artery, which can lead to renal ischemia and kidney dysfunction.

One disease in which vascular diseases and their complications are very common is diabetes mellitus. Diabetes mellitus causes a variety of physiological and anatomical irregularities, the most prominent of which is the inability of the body to utilize glucose normally, which results in hyperglycemia. Chronic diabetes can lead to complications of the vascular system which include atherosclerosis, abnormalities involving large and medium size blood vessels (macroangiopathy) and abnormalities involving small blood vessels (microangiopathy) such as arterioles and capillaries.

Patients with diabetes mellitus are at increased risk of developing one or more foot ulcers as a result of established long-term complications of the disease, which include impaired nerve function (neuropathy) and/or ischemia. Local tissue ischemia is a key contributing factor to diabetic foot ulceration.

In addition to large vessel disease, patients with diabetes suffer further threat to their skin perfusion in at least two additional ways. First, by involvement of the non-conduit arteries, which are detrimentally affected by the process of atherosclerosis, and secondly, and perhaps more importantly, by impairment of the microcirculatory control mechanisms (small vessel disease). Normally, when a body part suffers some form of trauma, the body part will, as part of the body's healing mechanism, experience an increased blood flow. When small vessel disease and ischemia are both present, as in the case of many diabetics, this natural increased blood flow response is significantly reduced. This fact, together with the tendency of diabetics to form blood clots (thrombosis) in the microcirculatory system during low levels of blood flow, is believed to be an important factor in ulcer pathogenesis.

Neuropathy is a general term which describes a disease process which leads to the dysfunction of the nervous system, and is one of the major complications of diabetes mellitus, with no well-established therapies for either its symptomatic treatment or for prevention of progressive decline in nerve function.

The thickening and leakage of capillaries caused by diabetes primarily affect the eyes (retinopathy) and kidneys (nephropathy). The thickening and leakage of capillaries caused by diabetes are also associated with skin disorders and disorders of the nervous system (neuropathy).

The eye diseases associated with diabetes are nonproliferative diabetic retinopathy, proliferative diabetic retinopathy, diabetic maculopathy, glaucoma, cataracts and the like.

Other diseases, although not known to be related to diabetes are similar in their physiological effects on the peripheral vascular system. Such diseases include Raynaud syndrome, CREST syndrome, autoimmune diseases such as erythematosis, rheumatoid disease, and the like.

As used herein, the term "peripheral vascular diseases" comprises any peripheral vascular disease including peripheral and autonomic neuropathies. Examples of "peripheral vascular disease" include peripheral arterial disease, such as chronic arterial occlusion including arteriosclerosis, arteriosclerosis obliterans and thromboangiitis obliterans (Buerger's disease), macroangiopathy, microangiopathy, diabetes mellitus, thrombophlebitis, phlebemphraxis, Raynaud's disease, Raynaud's syndrome, CREST syndrome, health hazard due to vibration, Sudeck's syndrome, intermittent claudication, cold sense in extremities, abnormal sensation in extremities, sensitivity to the cold, Meniere's disease, Meniere's syndrome, numbness, lack of sensation, anesthesia, resting pain, causalgia (burning pain), disturbance of peripheral circulation function, disturbance of nerve function, disturbance of motor function, motor paralysis, diabetic peripheral circulation disorder, lumbar spinal canal stenosis, diabetic neuropathy, shock, autoimmune disease such as erythematosis, rheumatoid disease and rheumatoid arthritis, autonomic neuropathy, diabetic autonomic neuropathy, autonomic imbalance, orthostatic hypotension, erectile dysfunction, female sexual dysfunction, retrograde ejaculation, cystopathy, neurogenic bladder, defective vaginal lubrication, exercise intolerance, cardiac denervation, heat intolerance, gustatory sweating, diabetic complication, hyperglycemia, hypoglycemia unawareness, hypoglycemia unresponsiveness; glaucoma, neovascular glaucoma, cataract, retinopathy, diabetic retinopathy, diabetic maculopathy, occlusion of retinal artery, obstruction of central artery of retina, occlusion of retinal vein, macular edema, aged macular degeneration, aged disciform macular degeneration, cystoid macular edema, palpebral edema, retinal edema, chorioretinopathy, neovascular maculopathy, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, damage of skin, skin ulcer including foot ulcer, diabetic ulcer, burn ulcer, lower leg ulcer, postoperative ulcer, traumatic ulcer, ulcer after herpes zoster, radiation ulcer, drug induced ulcer, frostbite (cold injury), chilblain, gangrene and sudden gangrene, angina pectoris/variant angiitis, coronary arteriosclerosis (chronic ischemic heart disease, asymptomatic ischemic heart disease, arteriosclerotic cardiovascular disease), myocardial infarction, heart failure, congestive heart failure and painless ischemic heart disease, pulmonary edema, hypertension, pulmonary hypertension; portal hypertension, diabetic nephropathy, decubitus, renal failure.

Cortisol

The estimated daily cortisol production rate in normal subjects varies between 4-15 mg/m$^2$ per day or, according to more recent studies between 9 and 11 mg/m.sup.2 per day. In order to describe the 24-hour variation in serum cortisol levels adequately, the day may be divided into, for example, four phases. Phase 1 is a 6-hours period of minimal secretory activity 4 h before and 2 h after onset of sleep. Phase 2 refers to the 3rd to 5th hours of sleep when there is a preliminary nocturnal secretory episode. Phase 3 is a 4-hour main secretory phase during the last 3 h of sleep and the first hour after wakening. Phase 4 is an 11-hour phase of intermittent secretory activity when there is a slow decline in serum levels of cortisol.

In a study by Mah et al. (Clinical Endocrinology (2004) 61, 367-375) the circadian rhythm of serum cortisol of normal subjects is described. Peak levels of about 400-800 mmol/l, about 150-300 mmol/l and about 150 mmol/l are observed at about 6 am, 2 pm and 9 pm, respectively, and the lowest level is about midnight. In this study it is observed that the endogenous cortisol levels reach their highest levels within 30 minutes after wake-up. In order to mimic the circadian rhythm, Mah et al. recommend a thrice-daily treatment regimen of hydrocortisone, the first dose taken in the fasted state and delaying the breakfast 1-3 hours and the other two doses taken 15-60 min before food. A trice-daily regimen is also recommended in a recent review by Czock et al. (Clin. Pharmacokinet (2005) 44, 61-98) due to the short half-life of hydrocortisone, and for prednisolone a twice-daily regimen is preferred over a once-daily regimen.

Cortisol Test

The absence of rapid response and inexpensive testing for cortisol has, heretofore, prevented the linking of GCR antagonists (e.g., ORG 34517) to a cortisol pre-test for entry into clinical trials for GCR antagonists and will inhibit the ability to select the patients most likely to receive the benefit of treatment with the compounds when available for clinical use. The invention provides the pairing of an affordable, real-time cortisol test (e.g., PopTest Cortisol) which will enable the successful completion of clinical trials for this class of drugs as well as form the basis for their future, anticipated therapeutic use(s).

Conditions that may be treated using, for example, a linked salivary cortisol quantification test and GCR antagonist (e.g., ORG 34517) system include, but are not limited to the following:

Major Depressive Disorder (MDD)

MDD is a psychiatric disorder which has a lifetime prevalence of around 8%. One of the most consistent findings in psychiatry is that patients with major depression present with alterations in the hypothalamic-pituitary-adrenal (HPA) axis. A significant percentage of depressed patients exhibit hypersecretion cortisol, as manifested by elevated plasma, cerebrospinal fluid, and salivary concentrations of cortisol and increased urinary free cortisol. In addition, many depressed patients exhibit a clear inability to switch off endogenous cortisol release following exogenous challenge with the potent synthetic glucocorticoid dexamethasone (the so-called dexamethasone non-suppressors) (Gold P. W., et al., Clinical and biochemical manifestations of depression: relation to neurobiology of stress. New England J. Med. 319, 413-420, 1988). This 'sub-group' of severely compromised patients are most often the ones in whom depression becomes a life-threatening illness that warrants hospitalization.

Other abnormalities of the HPA axis found in depressed patients are increased cortisol response to corticotrophin, a blunted corticotrophin response to CRH (corticotrophin releasing hormone), and adrenal and pituitary enlargement (for a review see Holsboer, F. and Barden, N.: Endocrine Reviews 1996, 17, 187-205). These observations have been interpreted to suggest a causal relationship between disturbed functioning of the HPA axis and the pathology of depression (Murphy, B. E. P. J. of Steroid Biochem. and Mol. Biol. 1991, 38, 537-559). Therapeutic efficacy of classical antidepressants has been shown to be preceded by or to coincide with restoration of the disturbed HPA axis in depression (Holsboer and Barden, 1996, supra). It has been postulated that any intervention which can restore this HPA dysfunction may have antidepressant potential.

One type of such intervention, studies of which support the impression that HPA-axis functioning and high circulating cortisol is a major instigator of major depression is the administration of glucocorticoid synthesis inhibitors, as has been shown in patients suffering from Cushing's Syndrome, which is a condition in which high cortisol levels are reported as a result of adrenal gland malfunction (due to a pituitary tumour or a secondary tumour, both producing the cortisol secretagogue ACTH). The depressive symptoms associated with Cushing's disappear relatively quickly with the return of cortisol levels to normal. Such treatment may involve removal of the offending tumour or treatment with cortisol synthesis inhibitors such as metyrapone, ketoconozole, or aminoglutethimide (Murphy, B. E. P., Steroids and Depression. J. Steroid Biochem & Mol. Biol. 38, 537-558, 1991). Similarly, relatively recent clinical trials have demonstrated that cortisol synthesis inhibitors can be used to ameliorate depressive symptoms in severe, treatment-resistant non-Cushing depressives (Murphy, B. E. P., Can. J. Psych. 43, 279-286, 1998; see also U.S. Pat. No. 4,814,333 (Ravaris, C. L.)).

Another type of intervention is the use of direct GCR antagonists, which have much more specific pharmacological effects as compared to synthesis inhibitors and which may help restore HPA activity Small scale pilot clinical studies have been conducted in order to study the antidepressant activity of the non-selective glucocorticoid receptor antagonist RU 486 (mifepristone; Murphy, B. E. P. et al. J. Psychiat. Neurosc. 18, 209-213, 1993). More recently (Nemeroff, C., Remeron Scientific Expert Meeting, Budapest, Mar. 29-Apr. 1, 2001) it was demonstrated in a Phase IIB continuation of this study, that both the number of responders as well as the efficacy of the psychosis treatment increased with increasing daily dose of mifepristone as measured by the change in Brief Psychiatric Rating Scale (50 mg-33% change; 600 mg-40% change and 1200 mg-52% change). These data indicate that a higher dose of glucocorticoid receptor antagonist is correlated with a higher clinical efficacy.

Non-response to standard treatments, however, reach levels as high as 50%. (Connolly K R, Drugs. 2011; 71: 43-64.) Frequently, extra interventions are necessary to get patients to achieve remission. Various augmentation and combination strategies have been described in the literature for difficult to treat major MMD patients.

Use of an HPA-axis modulating drug in these patients has not been studied in spite of the fact that there is clear evidence that at least a sub-group of MDD patients have significant HPA-axis dysfunction, as noted above. Biological symptoms, indicative of excessive activity of the HPA-axis, have been reported with great consistency. In parallel, there is a body of evidence suggesting that there is an association between HPA-axis functioning and treatment response, where high HPA-axis activation at baseline, or post-treatment, is associated with a poorer response to SSRI treatment or a higher relapse risk.

Preclinical studies indicate that HPA-axis dysfunction of the type seen in affective disorders can attenuate the neurochemical effects of a selective serotonin re-uptake inhibitor (SSRI) antidepressant. Conversely, in animals with normal HPA axis function, co-administration of GR antagonists augmented the neurochemical effects of an S SRI. These data provide a mechanistic underpinning of the GR antagonist augmentation strategy, and moreover indicate that the strategy may prove efficacious in patients both with and without HPA axis dysfunction.

Small scale pilot clinical studies were conducted in order to study the antidepressant activity of the non-selective glucocorticoid receptor antagonist RU 486 (mifepristone; Murphy, B. E. P. et al. J. Psychiat. Neurosc. 18, 209-213, 1993). A double blind, 4 week, paroxetine controlled study of ORG 34517 in depressed patients was carried out. Paroxetine is a selective serotonin re-uptake inhibitor which is recognized as an effective antidepressant for major depression. Patients were selected which had a primary depressive disorder fulfilling the diagnostic criteria of a MDD as defined by the DSM-IV for recurrent (296.3) episodes, and who had a severity of depression which resulted in a total score of at least 22 on the HAMD-21 (Hamilton Rating Scale for Depression; see Hamilton, M. "A rating scale for depression." J. Neurol. Neurosurg. Psychiat. 1960, 23, 56-62) scale at baseline. Patients had an episode of depression which had lasted at least 2 weeks before baseline.

In this study, patients were randomly allocated to one of three treatment groups. Group I patients (50 patients) received 2 capsules with 75 mg of ORG 34517 and one placebo (total daily dose 150 mg) for the first 2 weeks and 2 capsules with 75 mg ORG 34517 and 1 capsule with 150 mg (total daily dose 300 mg) the next 2 weeks; Group II patients (46 patients) received 3 capsules with 150 mg ORG 34517 (total daily dose 450 mg) in the first 2 weeks and 4 capsules of ORG 34517 (total daily dose 600 mg) in the next 2 weeks; Group III patients (44 patients) received 2 capsules with 10 mg paroxetine and one placebo capsule (total daily dose 20 mg) for the first 2 weeks, followed by 2 capsules of 10 mg and one capsule of 20 mg paroxetine (total daily dose 40 mg) in the next 2 weeks. Medication was administered orally in the morning. Efficacy assessment was done on days 4, 7, 10, 14, 21, 28 and 35 by using the 21-item HAMD scale.

Thus, GCR antagonist therapy could prove a useful mechanism for treatment of selected individuals who fail to respond to current anti-depressant therapies such as SSRIs, providing a way to enhance responsiveness or as an alternate means of achieving a maintained euthymia.

Psychotic Depression

Psychotic major depression has long been recognized as a distinct psychiatric illness, having both psychotic and depressive components in a differential diagnosis. Psychotic major depression is very common. It has been estimated that twenty five percent of depressed patients admitted to the hospital have psychotic major depression (Coryell (1984) J. Nerv. Ment. Dis. 172:521). Like major depression, psychotic depression is often also a result of high circulating cortisol levels. Various evidence supports this concept. Psychosis has been associated with Cushing's syndrome (Gerson (1985) Can. J. Psychiatry 30:223-224; Saad (1984) Am. J. Med. 76:759-766). A GR antagonist has been used to treat acute psychiatric disturbances secondary to Cushing's syndrome. One study showed that a relatively high dose of such a GR antagonist (400 to 800 mg per day) was useful in rapidly reversing acute psychosis in patients with severe Cushing's' Syndrome due to adrenal cancers and ectopic secretion of ACTH from lung cancer (Van der Lely (1991) Ann. Intern. Med. 114:143; Van der Lely (1993) Pharmacy World & Science 15:89-90; Sartor (1996) supra). Relatively high dose mifepristone, in the range of 8-12 mg/kg/day, over a relatively short period of time (4 days), was also shown to be effective in the treatment of psychosis associated with psychotic major depression (International Patent Application WO 99/17779; Schatzberg and Belanoff).

Surgery-Associated Immune Suppression in the Elderly.

In healthy, young to middle aged subjects suffering from stress, there is a physiological balance between pro-inflammatory and anti-inflammatory mediators. In the elderly, the immune response is blunted as a result of the decline in several components of the immune system (immune senescence) and a shifting to a chronic pro-inflammatory status (the so-called "inflammaging" effect (Butcher and Lord, (2004) Aging Cell, pp. 151-160). As production of cortisol remains reasonably constant with age, whereas summed levels of DHEA and DHEAS decrease gradually from the third decade, reaching 10-20% of their maximum by the eighth decade, Butcher and Lord (2004, supra) propose a model for age and stress, in which the age-related increase in the ratio of cortisol to DHEAS, combined with an elevated cortisol release during stress, leads to a significant reduction of immunity in aging subjects. This is proposed to explain that aging subjects are far more prone to infections under conditions of stress. (Butcher and Lord (2004, supra); Butcher et al. (2005, Aging Cell 5, pp. 319-324).

The present invention relates to the use of a GCR antagonist for the prevention or treatment of infections or infectious conditions, in an aging patient, such as a human subject. The beneficial effects of said GCR antagonists may be explained on the basis of their correcting influence on the cortisol/DHEA(S) ratio. It is believed that the effect in selected subjects, found to have high circulating cortisol by a saliva test as provided for by this invention, can be explained by the unbalanced immunosuppressive role of the increased cortisol/DHEAS ratio in the aged group in comparison to the balanced influence of cortisol and DHEAS on the immune system in normal subjects.

The meaning of the term 'aging subject' or 'aged subject' will be well understood in the context of the use according to this invention. Although it is not linked to an exact lower age limit this general notion refers in the human situation usually to a person of at least 55 years old, but it is more clear with a lowest age limit set at 60, 65, 70 or 75 years.

In the context of the invention, the infection or infectious condition can be caused by any of several agents, e.g., by bacteria, by viruses or by fungi. Also in the context of the present invention, the expression "infectious conditions" means silent or subclinical infections as well as conditions not resulting in a manifest infectious disease, but in which at least one parameter associated with an infectious disease, such as the white blood (e.g., neutrophil, basophil or eosinophil) cell counts or the level of some antibodies or some cytokines is higher than normal. Normal values are known to the expert and may be found in standard medical manuals.

Particular uses according to the invention relate to aging subjects suffering from an infection or an infectious condition concomitant to stress resulting from a trauma. The invention particularly relates to uses wherein the subject suffers from the consequences of a bone fracture and/or bone surgery, either for such injury or for joint replacement for osteoarthritis or rheumatoid arthritis. The invention also relates to uses wherein the subject suffers from an infection or an infectious condition concomitant to psychological stress, particularly acute emotional stress.

Post-Traumatic Stress Disorder (PTSD)

PTSD is a severe anxiety disorder that can develop after exposure to any event that results in psychological trauma. This event may involve the threat of death to oneself or to someone else, or to one's own or someone else's physical, sexual, or psychological integrity, overwhelming the individual's ability to cope. As an effect of psychological trauma, PTSD is less frequent and more enduring than the more commonly seen acute stress response. Diagnostic symptoms for PTSD include re-experiencing the original trauma(s) through flashbacks or nightmares, avoidance of stimuli associated with the trauma, and increased arousal, such as difficulty falling or staying asleep, anger, and hyper-vigilance. Formal diagnostic criteria (both DSM-IV-TR and ICD-9) require that the symptoms last more than one month and cause significant impairment in social, occupational, or other important areas of functioning. (Diagnostic and statistical manual of mental disorders: DSM-IV. American Psychiatric Association. 1994. Washington, D.C.: American Psychiatric Association.)

PTSD displays biochemical changes in the brain and body that differ from other psychiatric disorders such as major depression. Abundant evidence suggests derangement of HPA-axis physiology in individuals diagnosed with PTSD, though the nature of the derangements is variable: some have low cortisol, some have normal levels, others have high levels of cortisol and for some, levels may be normal, but circadian rhythm is lost. It is postulated that these reflect different baseline mechanisms, but that when cortisol is high, either in a sustained way through the day or by loss of circadian rhythm with elevated night time levels, it is likely to be an important component of the clinical symptomatology (Lindley S E, et al. Basal and dexamethasone suppressed salivary cortisol concentrations in a community sample of patients with posttraumatic stress disorder. Biol. Psychiatry 2004; 55: 940-5). In such patients, determined by salivary cortisol testing, administration of a GCR antagonist is expected to be therapeutic or beneficial for the symptoms of PTSD.

Prevention of Weight Gain in Patients Using Anti-Psychotic and Anti-Depressant Medications Anti-psychotic and some anti-depressant medications (e.g., SSRIs) are amongst the most important tools for treating psychiatric conditions of all kinds. However, management of patients on who take many of these medications for chronic, long term disease is made difficult by their significant side effect profiles. One of the most important of these is weight gain and the attendant metabolic syndrome that follows. For example, it is estimated that 40-80% of patients who are under chronic anti-psychotic administration experience substantial weight gain, often exceeding 20% or more over their ideal body weights (Umbricht et al. J Clin. Psychiatry 1994; 55: 157-160; Khan A Y, et al. J Psychiatr Pract. 2010; 16: 289-96; Pramyothin P, Khaodhiar L. Curr Opin Endocrinol Diabetes Obes. 2010; 17: 460-6.; Rummel-Kluge C et al. Schizophr Res. 2010; 123: 225-33). Such weight gain is one of the most common causes of poor compliance with anti-psychotic and anti-depressant regimens and, therefore, of long term failure of therapy. Furthermore, anti-psychotic medications specifically are commonly associated with development of insulin resistance and metabolic syndrome (with development of type 2 diabetes mellitus and hyper/dyslipidemia states) and the potentially and significantly increased risks for cardiovascular disease; these conditions are of tremendous medical consequence for patients who are thereby caught in a "can't live with them, can't live without them" treatment scenario. While weight gain is potentially seen with all anti-psychotic medications, they are particularly common and tend to more severe with the newer or "atypical" AP drugs (Allison et al. Am J Psychiatry 1999; 156:1686-1696; Rummel-Kluge C et al. Schizophr Res. 2010; 123: 225-33).

Elevations in cortisol are associated with changes in body fat and insulin resistance. Several years ago, in a proof of principle clinical experiment, it was reported that one GCR anatogonist (mifepristone) was a highly effective treatment for multiple medical complications in a patient with Cushing's disease whose illness had not responded to surgery and radiation, including reversal of insulin dependent diabetes: the patient was able to stop insulin within a month (Chu et al., J. Clin. Endocrinol. Metab. 2001; 86, 3568-3573.). These data suggest that a GCR antagonist could be useful for blocking and reversing the insulin resistance and weight changes seen in some patients treated with atypical antipsychotic agents. To this end, this compound was tested in rats who had olanzapine-induced weight gain and increases in abdominal fat; reversal of weight gain was seen and reduction of abdominal fat was obtained (Beebe et al. Behav. Brain Res. 2006; 171, 225-229). A clinical trial with this compound then confirmed this benefit in humans with a 2 week study of 600 mg/day of mifepristone that reduced olanzapine-induced weight gain in 57 non-overweight healthy males with Body Mass Indices less than 25 (Gross et al., Adv Ther. 2009; 26: 959-69.). Thus, GCR antagonist therapy could prove a useful mechanism to target in treating psychotic patients with atypical antipsychotic agents.

Cushing's Syndrome

Cushing's Syndrome is a set of conditions in which high levels of circulating cortisol or other GCR agonists cause a set of seriously debilitating and sometimes life threatening signs and symptoms including, but not limited to, psychiatric disturbances (e.g. anxiety, depression, psychosis), immunosuppression, insulin resistance and metabolic syndrome, skin conditions, hypertension and osteoporosis. Endogenous cortisol may be produced by ACTH-secreting, benign or malignant tumors of the pituitary gland ("Cushing's Disease") or of the adrenal cortex. These are rare conditions and therefore Cushing's Syndrome is considered an "orphan disease."

A proof of concept trial using RU486 to treat patients with tumor-related Cushing's Syndrome demonstrated efficacy in remitting symptoms such as glucose metabolic abnormalities (i.e., glucose intolerance; (group 1) and hypertension (group 2). Statistically significant improvement was achieved for both groups: with 60% responding in the glucose intolerant group and 43% in the hypertensive group (Corcept Therapeutics Press Release Dec. 22, 2010). Thus, GCR antagonist therapy can be expected to provide clinical benefits for patients with Cushing's Syndrome administered prior to tumor surgery to improve surgical outcomes and/or post-surgery to mitigate symptoms in patients for whom surgical cure is not achievable.

In addition, GCR antagonist therapy can be expected to provide clinical benefits for patients, for example, in hospitals, nursing homes, nurseries, daycares, schools, work environments, public transportation, healthcare settings, psychiatric institutions, and long-term nursing facilities.

Diagnostic Systems and Kits

A diagnostic kit may comprise some or all of the following components: 1) one or more standards comprised of one or more of the biomarker(s) of the invention, such as cortisol; 2) a ligand, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a ligand carrier, such as an antibody carrier, for example, a lateral flow device, or a microplate with bound antibody, or polystyrene beads.

An example of such a kit is a quantitative ELISA (enzyme-linked immunosorbent assay) that determines the concentration or concentrations of the biomarker or biomarker(s) in accordance with methods embodied by the invention. The principle of the assay is to use the quantitative sandwich enzyme immunoassay technique wherein a monoclonal or polyclonal antibody selective for a biomarker is pre-coated onto a carrier such as a microplate into its wells. The standards and sample are then pipetted into the wells and any of the biomarker that is present is bound to this immobilized antibody. Next, the wells are washed with washing buffer, and an enzyme-linked monoclonal or polyclonal antibody that is specific for the biomarker is added to the wells. Washing is again performed, then a substrate solution is added to the wells. Color subsequently develops in proportion to the amount of polypeptide of the invention that is bound in the first step. The color development is stopped using a stop solution, and the intensity of the color is measured by a microplate reader.

The methods of the invention may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced form one location on the carrier to another. There are many formats of lateral flow assays suitable for use in a method embodied by the invention, and the skilled person will readily know how to select and optimize a particular format. An example of a lateral flow test strip of the invention comprises, for example, the following components:

1. Sample pad—an absorbent pad onto which the test sample is applied.
2. Conjugate or reagent pad—this contains antibodies specific to the target analyte conjugated to colored particles (usually colloidal gold particles, or latex microspheres).
3. Reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies).
4. Wick or waste reservoir—a further absorbent pad designed to draw the sample across the reaction membrane by capillary action and collect it.

Double antibody sandwich assays—In this format the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Double antibody sandwich assays are most suitable for larger analytes, such as bacterial pathogens and viruses, with multiple antigenic sites. Competitive assays are primarily used for testing small molecules and differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone, an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. Competitive assays are most suitable for testing for small molecules, such as mycotoxins, unable to bind to more than one antibody simultaneously. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

Quantitative tests—While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan® lateral flow reader for use with its range of Reveal® assay kits and Charm Sciences also supplies a reader for its Rosa® range of mycotoxin test strips. More sophisticated techniques, such as fluorescent dye labeled conjugates, have also been developed to improve the quantitative potential of lateral flow assays. Applications in the 20 years since the first lateral flow test was launched have expanded to include a huge range of different tests that have been developed based on the same technology. The first commercially available kits were aimed at the clinical diagnostics field, but there are now products with applications in almost every branch of microbiology. Clinical microbiology—lateral flow tests have been developed for bacterial pathogens, respiratory and enteric viruses, intestinal parasites and bacterial toxins.

Many of the lateral flow immunoassay products designed for the clinical sector were intended to be used at the point-of-care for direct testing of fecal, blood and urine samples and nose and throat swabs, where the simple operation and speed of the tests is key to their use outside of the laboratory. However, the same test strips may also be useful as a quick confirmatory test following laboratory culture of clinical samples. Food and agricultural microbiology—test strips are available for food borne bacterial pathogens, bacterial and fungal toxins. In the food microbiology sector, the main applications are more likely to be in the laboratory, although there are field test kits for mycotoxins in grain samples. Testing for food borne bacterial pathogens generally involves at least one enrichment stage before the assay strip is used to confirm the presence or absence of the pathogen. Some manufacturers, such as Dupont®, have developed enrichment media and methods specifically designed for use with lateral flow test strips. Test strips may also be useful for rapid confirmation of the identity of bacterial isolates from conventional microbiological testing.

A diagnostic system in kit form of the present invention includes, for example, in an amount sufficient for at least one assay, a polypeptide, antibody composition or monoclonal antibody composition of the present invention, as a packaged reagent. Instructions for use of the packaged reagent are also typically included.

A diagnostic system in kit form of the present invention may include, for example, a means for detecting the presence of a biological substance in a test sample, comprising for example, a lollipop-like apparatus including a stem integrated with the base and a head integrated with the stem, for collecting a test sample consisting of, for example, saliva, or a bodily fluid sample from a subject. The stem head may include a receptor of a sponge like carrier to ensure a high void volume to absorb sufficient saliva, or bodily fluid sample. See U.S. Pat. No. 7,993,283, incorporated by reference herein in its entirety.

A diagnostic system in kit form of the present invention may include, for example, a means for combining the test sample with a buffering system (Reagent 1) containing viscosity controllers and stabilizers into a reaction vessel and mixing the solution. A diagnostic system in kit form of the present invention may include, for example, a means for reading the a parameter of the reaction vessel with sample and buffer, and further means for combining the test sample and buffer mixture with a fluorescence-labeled ligand (Reagent 2) to said biological substance in the reaction vessel, mixing the solution to produce an assay solution. Furthermore, Reagent 2 may be delivered to the reaction vessel without further dilution volume of the assay solution.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is .sup.125I. Another group of useful labeling means are those elements such as .sup.11C, .sup.18F, .sup.15O and .sup.13N which themselves emit positrons. The positrons so emitted produce gamma rays upon encounters with electrons present in the animal's body. Also useful is a beta emitter, such $^{111}$indium or $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of cortisol in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of, for example, cortisol. Such a system comprises, in kit form, a package containing an antibody to, for example, cortisol.

"Sample" refers to, for example, essentially any source from which materials of interest to be analyzed (e.g., ligands and antiligands, such as antibodies and antigens, and nucleic acids and their complements) can be obtained. A sample may be acquired from essentially any organism, including animals and plants, as well as cell cultures, recombinant cells and cell components. Samples can be from a biological tissue, fluid or specimen and may be obtained from a diseased or healthy organism. Samples may include, but are not limited to, saliva, sputum, amniotic fluid, blood, blood cells (e.g., white cells), urine, semen, peritoneal fluid, pleural fluid, tissue or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Alternatively, a biological sample may be obtained from a cell or blood bank where tissue and/or blood are stored, or from an in vitro source, such as a culture of cells. Techniques for establishing a culture of cells for use as a source for biological materials are well known to those of skill in the art.

In one embodiment the sample is selected from or is derived from, for example, microbial products or biological products.

Although the above described example relates to the antigens relating to disease, the immunoassay apparatus could be used, for example, as an allergy test kit, as a test kit for drugs of abuse or for analyzing non-human derived samples e.g. bovine, porcine, and veterinary tests.

Specific reagents used in the assay device will be selected so as to ensure that the particular target analyte is detected as is well known in the art. The target analyte may be any analyte for example a chemical reagent which may be organic or inorganic, and which optionally comprises a hapten, a protein, a polypeptide, a microorganism or a nucleic acid sequence.

In particular, the analyte is a hormone such as a fertility hormone like progesterone or a stress hormone such as cortisol. However, there is a wide range of applications of these types of tests across the entire field of diagnostics and analysis. Detection of marker proteins or hormones can be diagnostic of certain disease conditions in humans or animals, and the presence of drugs or drug residues may also be required to be detected, for example, in animal husbandry, forensic medicine or in the testing for banned or prohibited drug substances.

Alternatively, the analyte is a chemical reagent, for instance a small molecule, which suitably comprises a hapten. Small molecules will generally comprise a single recognizable binding site. Typically they will have a molecular weight of less than 1 kDa.

Where the assay utilizes a labelled binding partner for the analyte and the analyte is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, where the binding partner may comprise the acid part of the reactive pair.

Where the analyte is or comprises a hapten or a protein antigen, the binding partner may comprise an antibody or a binding fragment thereof, which may be monoclonal, polyclonal or recombinant, but preferably is monoclonal. Where the analyte is a hormone or enzyme, the labelled binding partner may comprise a labelled receptor for the analyte. However, where the analyte is itself an immunoglobulin, and in particular, an antibody, the labelled binding partner may also comprise for instance, an antigen or recombinant antigen, as well as anti-antibody immunoglobulin such as antisera.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

For example, where the analyte is a biologically active material such as an active agrochemical as discussed above, specific reagents used in the assay device will be selected so as to ensure that the particular target biologically active material is detected as is well known in the art. The biologically active material may be any active chemical such as an agrochemical, for example a chemical reagent which may be organic or inorganic, and which optionally comprises a hapten, a protein, a polypeptide, a microorganism or a nucleic acid sequence. Most preferably the biologically active material is a chemical reagent, for instance a small molecule, which suitably comprises a hapten. Small molecules will generally have a single antibody binding site. Typically they will have a molecular weight of less that 1 kDa.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

Microarrays

The method of the invention is particularly useful in combination with the analysis of gene expression profiles. In some embodiments, a gene expression profile, such as a collection of transcription rates of a number of genes, is converted to a projected gene expression profile. The projected gene expression profile is a collection of expression values. The conversion is achieved, in some embodiments, by averaging the transcription rate of the genes. In some other embodiments, other linear projection processes may be used.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natd. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997); U.S. Pat. No. 5,605,662.) Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

Using the methods of the invention a skilled artisan can readily select and prepare probes for a microarray wherein the microarray contains specific individual probes for less than all the genes in the genome and less than all the genes in the genome. In such embodiments, the microarray contains one or two or more individual probes, each of which hybridizes to an expression product (e.g., mRNA, or cDNA or cRNA derived therefrom) for a desired number of genes. Thus, for example, changes in the expression of all or most of the genes in the entire genome of a cell or organism can thereby be monitored by use of a surrogate and on a single microarray by measuring expression of the group of genes that are representative of all or most of the genes of the genome. Such microarrays can be prepared using the selected probes and are therefore part of the present invention.

Formulations

The compounds and compositions of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions and compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm).

"Stabilized" nanoparticles are nanoparticles coated with a stabilizing material and having a reduced tendency for aggregation and loss of dispersion with respect to nanoparticles of the compound of the invention without a stabilizing coating.

A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present invention can include nanoparticles, composite nanoparticles, nanosuspension, or nanocapsules of the present invention.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose.; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, Ill.) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Formulations for Alternate Specific Routes of Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The GCR antagonist may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases.

Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

Neoplasia Therapies

Any therapy (e.g., therapeutic or prophylactic agent) which is useful, has been used, is currently being used, or may be used for the prevention, treatment and/or management of neoplasia can be used to prevent, treat, and/or manage the patient whose neoplasia and/or cancer stem cells in accordance with the methods, compositions, and combinations of the invention. Also, neoplasia and/or cancer stem cell monitoring can be employed in conjunction with any therapy for cancer according to the instant invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, anti-angiogenesis therapies, targeted therapies, and/or biological therapies including immunotherapies and surgery. In certain embodiments, a prophylactically and/or therapeutically effective regimen comprises the administration of a combination of therapies. In certain embodiments, ORG 34517 can be administered as an agent to treat or prevent neoplasia, alone or in combination with, for example, neoplasia treating agents. In certain embodiments, RU486 (mifepristone) can be administered as an agent to treat or prevent neoplasia.

Examples of neoplasia agents or therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ORG 34517; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin $a_vb_3$ antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaglitazar, muraglitazar, peliglitazar, lobeglitazone, balaglitazone, ragaglitazar, rosiglitazone, farglitazar, sodelglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone;

compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer and/or cancer stem cells includes: i) antibodies, antibody fragments, and proteins that are either naked or conjugated to a therapeutic moiety that target certain cell surface targets on cancer stem cells, or ii) small molecules known in the art including ones that can be further optimized (e.g., via chemistry) or identified via a cancer stem cell-based screen (e.g., such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mcl-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that specifically bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) is not an anti-angiogenic agent.

In certain embodiments, the therapy(ies) is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine). In some embodiments of the invention, the therapy(ies) includes the administration cantharidin or an analog thereof. The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to alkylating agents, antimetabolites, plant alkaloids, cytotoxic agents, chemotherapeutic agents (e.g., a steroid, cytosine arabinoside, fluoruracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, *Pseudomonas* exotoxin, a bacterial endotoxin or the lipid A moiety of a bacterial endotoxin), growth modulators and RNase. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody or an antibody conjugated to a therapeutic moiety or an antibody fragment conjugated to a therapeutic moiety.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of IL-3R (i.e., the CD123 antigen). In other embodiments, the antibody, antibody-conjugate, antibody fragment, or antibody fragment-conjugate binds to the IL-3R, containing both the .alpha. and .beta. subunits. Methods for preparing antibodies to IL-3R and mimetics of antibodies to IL-3R are described in U.S. Pat. No. 6,733,743 B2, which is incorporated herein by reference in its entirety.

In other embodiments, the agent that binds to a marker on cancer stem cells is a ligand. In some embodiments, the ligand is a cytokine that binds to a cytokine receptor on cancer stem cells. In a particular embodiment, the ligand is interleukin-3 (IL-3) which can be conjugated to a therapeutic moiety that includes a chemotherapeutic agent, a plant-, fungus-, or bacteria-derived toxin, or a radionuclide. The IL-3-conjugate prophylactic and/or therapeutic therapy or regimen can be in the form of a recombinant fusion protein in embodiments where the conjugate is a toxin and the toxin is a protein, such as diphtheria toxin. Methods for preparing and isolating an IL-3-diphtheria toxin fusion protein (IL3DT) are described in Frankel et al., "Diphtheria toxin fused to human interleukin-3 is toxic to blasts from patients with myeloidleukemias," Leukemia 14:576 (2000) and Urieto et al., Protein Expression and Purification 33: 123-133 (2004), the disclosures of which are incorporated by reference in their entireties.

In certain embodiments, antibodies or fragments thereof that bind to a marker on cancer stem cells are substantially non-immunogenic in the treated subject. Methods for obtaining non-immunogenic antibodies include, but are not limited to, chimerizing the antibody, humanizing the antibody, and isolating antibodies from the same species as the subject receiving the therapy. Antibodies or fragments thereof that bind to markers in cancer stem cells can be produced using techniques known in the art. See, for example, paragraphs 539-573 of U.S. Publication No. 2005/0002934 A1, which is incorporated by reference in its entirety.

In some embodiments, the therapy comprises the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation based therapy. Non-limiting examples of such therapies include a chemotherapy and radiation therapy as described supra.

Currently available therapies and their dosages, routes of administration and recommended usage are known in the art and have been described in such literature as the Physician's Desk Reference (60th ed., 2006).

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two prophylactically and/or therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first prophylactically and/or therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

While the invention has been described in detail and with reference to specific examples thereof, it will be apparent to one skilled in the art that various changes and modifications can be made therein without departing from the spirit and scope thereof.

What is claimed is:

1. A method for treating a neurodegenerative disease in a patient in need of such treatment, said method comprising administering to the patient a therapeutically effective amount of ORG34517 ((11β,17β)-11-(1,3-benzodioxol-5-yl)-17-hydroxy-17-(1-propynyl) estra-4,9-dien-3-one), which has the following formula:

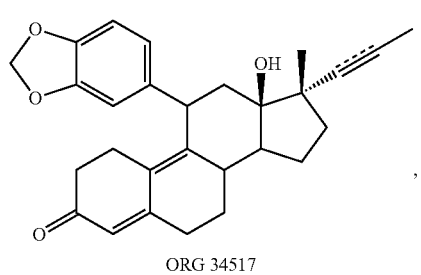

ORG 34517 wherein the neurodegenerative disease is selected from the group consisting of Parkinson's disease and multiple sclerosis.

* * * * *